US011763437B2

(12) United States Patent
Goto

(10) Patent No.: US 11,763,437 B2
(45) Date of Patent: Sep. 19, 2023

(54) ANALYZING APPARATUS AND METHOD, AND IMAGE CAPTURING SYSTEM

(71) Applicant: CANON KABUSHIKI KAISHA, Tokyo (JP)

(72) Inventor: Atsushi Goto, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 313 days.

(21) Appl. No.: 17/101,691

(22) Filed: Nov. 23, 2020

(65) Prior Publication Data
US 2021/0158502 A1 May 27, 2021

(30) Foreign Application Priority Data

Nov. 26, 2019 (JP) ................................. 2019-213650

(51) Int. Cl.
G06T 7/00 (2017.01)
G01N 33/02 (2006.01)
(Continued)

(52) U.S. Cl.
CPC ........... *G06T 7/0002* (2013.01); *G01N 33/02* (2013.01); *G06T 3/40* (2013.01); *G06T 7/001* (2013.01); *G06T 7/62* (2017.01); *G06T 2207/10016* (2013.01); *G06T 2207/20084* (2013.01); *G06T 2207/30128* (2013.01)

(58) Field of Classification Search
None
See application file for complete search history.

(56) References Cited

U.S. PATENT DOCUMENTS 5,286,980 A * 2/1994 Richert ..................... B07C 5/10
250/226
2016/0035093 A1* 2/2016 Kateb ................ G02B 21/0012
382/131
(Continued)

FOREIGN PATENT DOCUMENTS

CN 109509535 A * 3/2019 ............. G16H 20/60
JP 2004139141 A * 5/2004
(Continued)

OTHER PUBLICATIONS

Subhi, Mohammed Ahmed, Sawal Hamid Ali, and Mohammed Abulameer Mohammed. "Vision-based approaches for automatic food recognition and dietary assessment: A survey." IEEE Access 7 (Jan. 2019): 35370-35381. (Year: 2019).*

*Primary Examiner* — Emily C Terrell
*Assistant Examiner* — Nathan J Bloom
(74) *Attorney, Agent, or Firm* — Canon U.S.A., Inc. IP Division

(57) ABSTRACT

An analyzing apparatus extracts, from a food image, food information relating to types and served states of foods included in the food image and an edible portion of each food, calculates an area ratio between the edible portion of the same kind of food extracted from a plurality of food images acquired at different timings, stores conversion information for converting the area ratio into a volume ratio corresponding to each type and served state of food, and converts the area ratio of each food into a volume ratio using the stored conversion information corresponding to the food whose area ratio is to be converted from among the stored conversion information based on the food information.

10 Claims, 18 Drawing Sheets

(51) Int. Cl.
　　　*G06T 7/62*　　　(2017.01)
　　　*G06T 3/40*　　　(2006.01)

(56) References Cited

U.S. PATENT DOCUMENTS

2019/0282097 A1* 9/2019 Novotny ............ G09B 19/0092
2020/0365250 A1* 11/2020 Kim ..................... G06T 7/97

FOREIGN PATENT DOCUMENTS

| JP | 2005-250885 A | | 9/2005 |
|---|---|---|---|
| JP | 2005250885 A | * | 9/2005 |
| JP | 2008-204105 A | | 9/2008 |

* cited by examiner

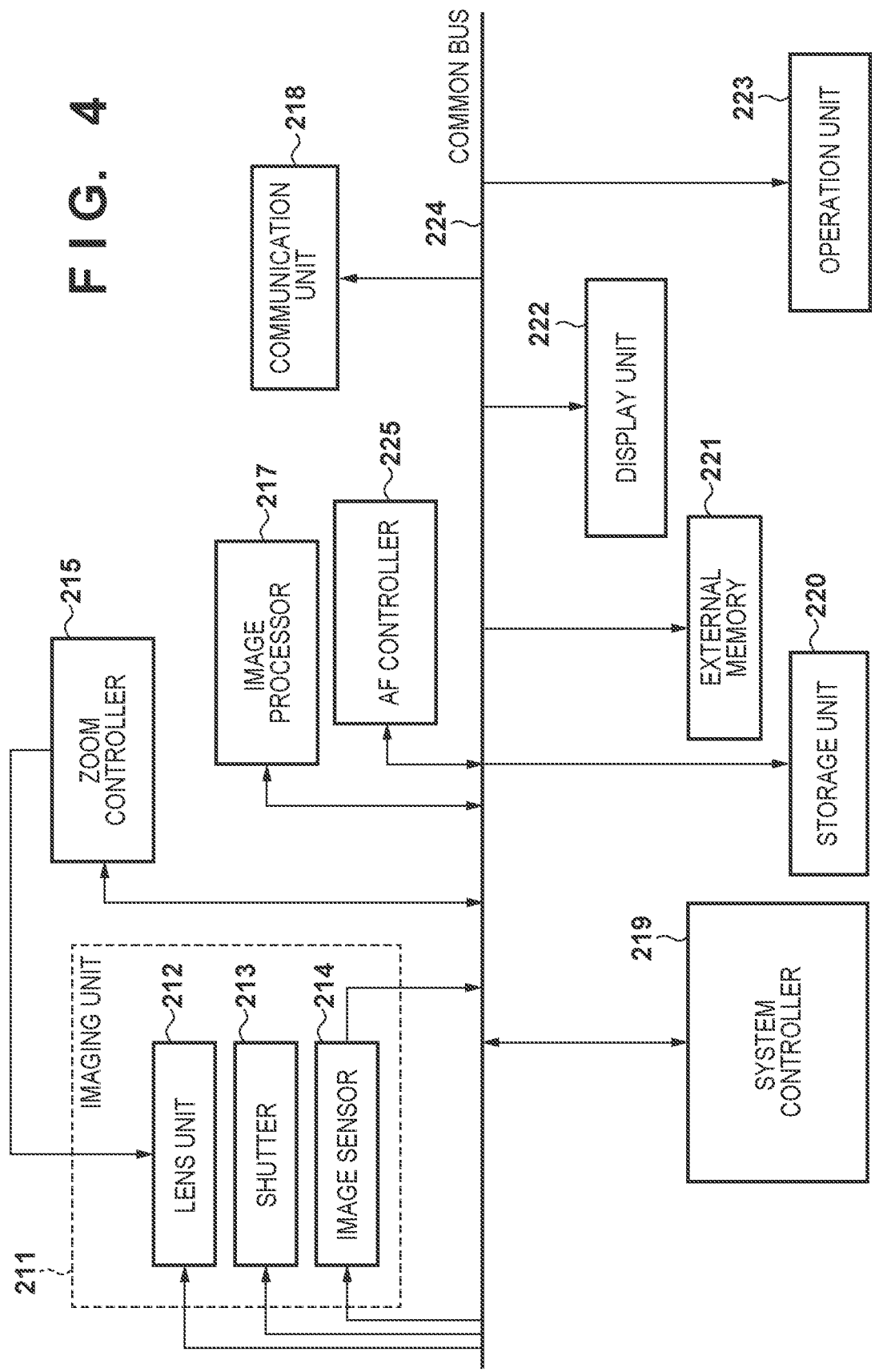

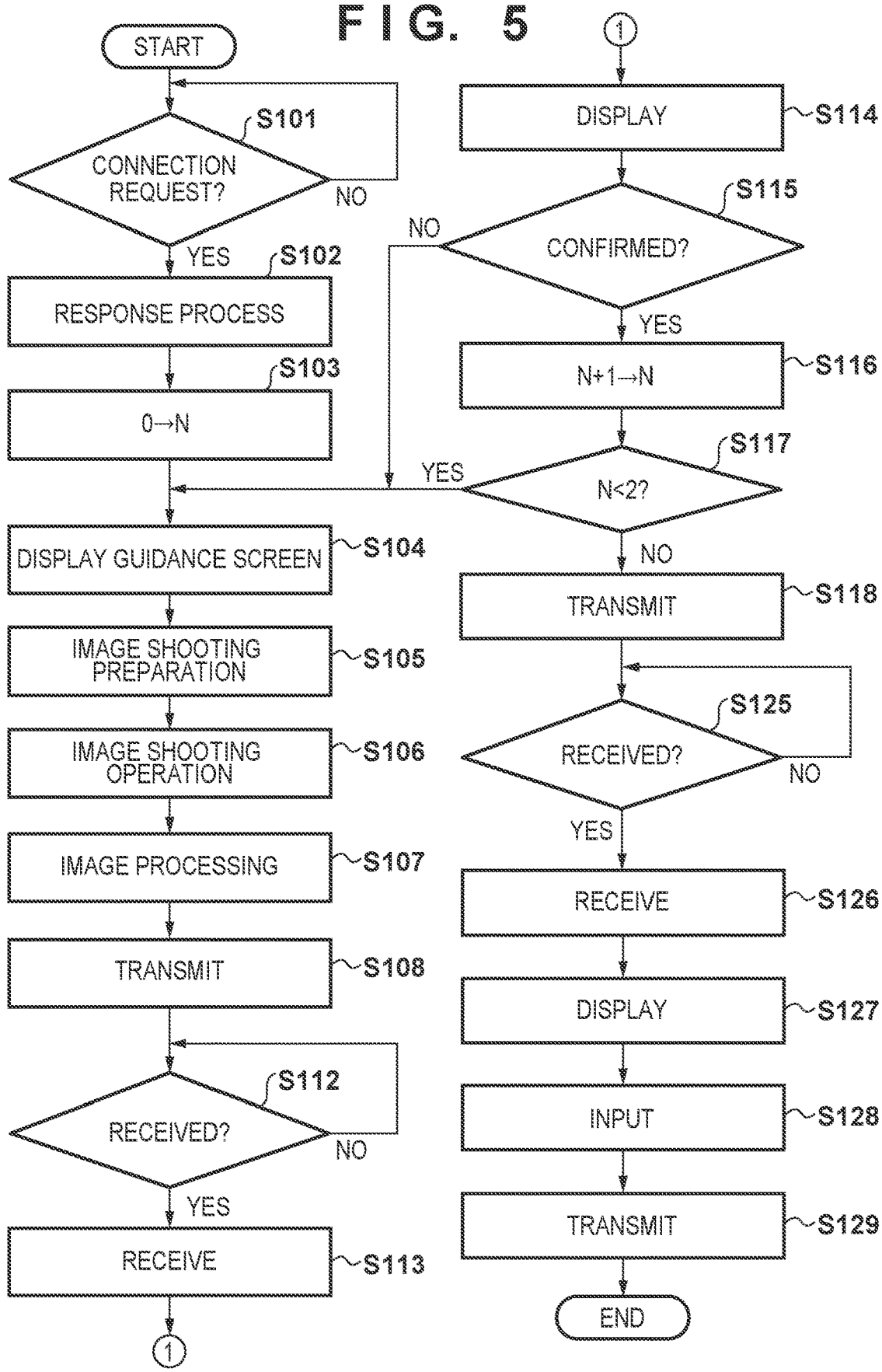

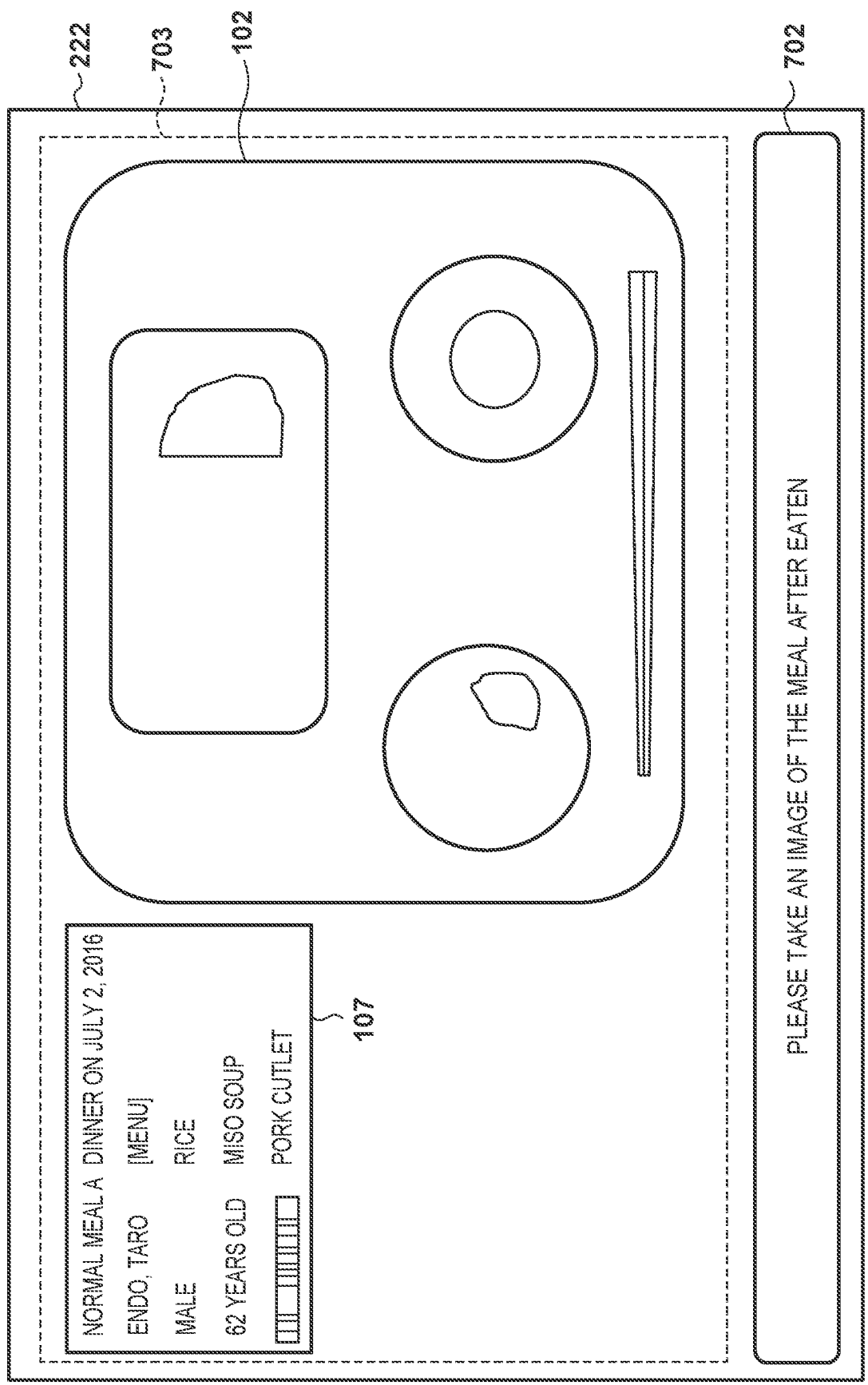

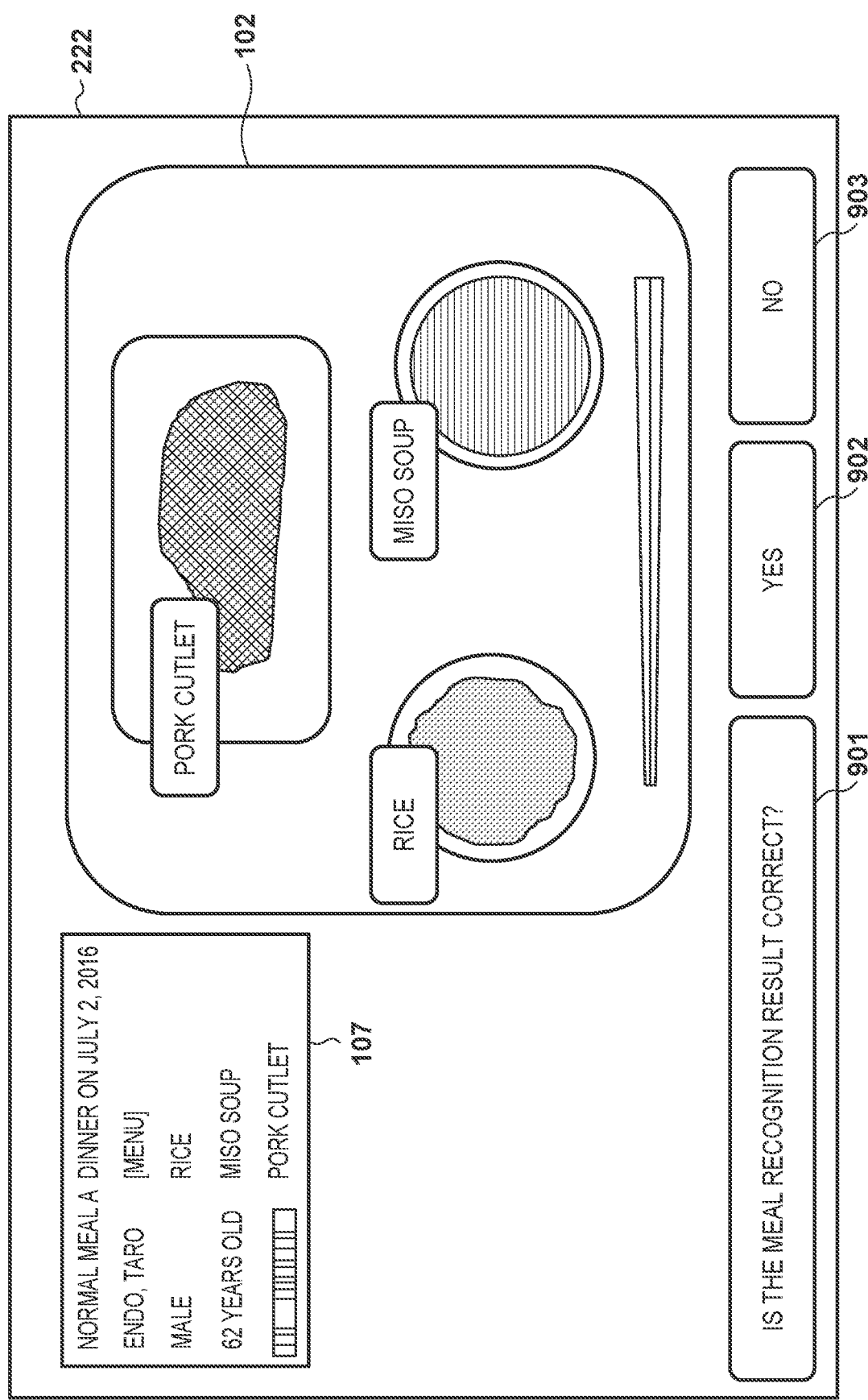

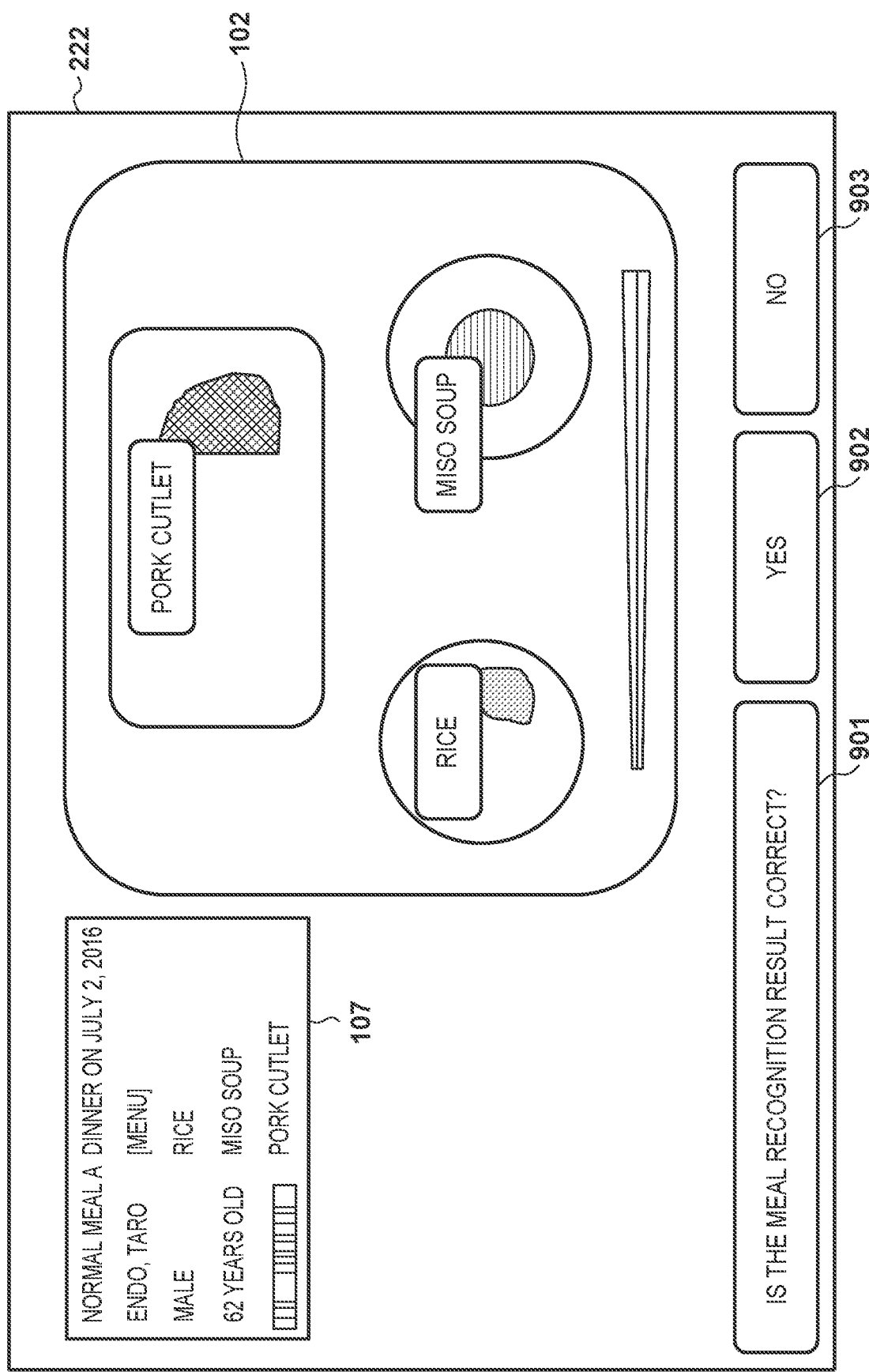

F I G. 10A (MEAL TABLE) ~1001

| MEAL ID | USER ID | MENU ID | DATE | TIME | BREAKFAST/LUNCH/DINNER |
|---|---|---|---|---|---|
| ... | ... | ... | ... | ... | ... |

(USER TABLE) ~1002

| USER ID | NAME | SEX | AGE | WARD | ROOM NUMBER |
|---|---|---|---|---|---|
| ... | ... | ... | ... | ... | ... |

(MENU TABLE) ~1003

| MENU ID | NAME OF THE MENU | FOOD INFORMATION ID (STAPLE) | FOOD INFORMATION ID (MAIN DISH) | FOOD INFORMATION ID (SIDE DISH 1) | FOOD INFORMATION ID (SIDE DISH 2) | FOOD INFORMATION ID (SOUP) | FOOD INFORMATION ID (DESSERT) | FOOD INFORMATION ID (OTHER) |
|---|---|---|---|---|---|---|---|---|
| ... | ... | ... | ... | ... | ... | ... | ... | ... |

(FOOD INFORMATION TABLE) ~1004

| FOOD INFORMATION ID | CLASSIFICATION | DISH ID | DISHWARE ID | INITIAL AMOUNT RATIO [%] | CONVERSION INFORMATION ID |
|---|---|---|---|---|---|
| ... | ... | ... | ... | ... | ... |

(DISH TABLE) ~ 1005

| DISH ID | FOOD NAME | STANDARD AMOUNT [GRAM] | CARBOHYDRATE [GRAM] | PROTEIN [GRAM] | LIPID [GRAM] | VITAMIN [GRAM] | MINERAL [GRAM] | DIETARY FIBER [GRAM] |
|---|---|---|---|---|---|---|---|---|
| ... | | | | | | | | |
| S002343 | PORK CUTLET | 400 | ... | | | | | |

(REMAINING AMOUNT INFORMATION TABLE) ~ 1006

| REMAINING AMOUNT INFORMATION ID | MEAL ID | FOOD INFORMATION ID | REMAINING AREA [%] | REMAINING VOLUME [%] | AMOUNT EATEN W.R.T. STANDARD AMOUNT |
|---|---|---|---|---|---|
| ... | ... | ... | ... | ... | ... |

(RESULT TABLE) ~ 1007

| REMAINING AMOUNT INFORMATION ID | MEAL ID | FOOD INFORMATION ID | NAME | FOOD NAME | STANDARD AMOUNT [GRAM] | AMOUNT EATEN [%] W.R.T. STANDARD AMOUNT | AMOUNT EATEN [GRAM] |
|---|---|---|---|---|---|---|---|
| ... | ... | ... | ... | ... | ... | ... | ... |

ANALYZING APPARATUS AND METHOD, AND IMAGE CAPTURING SYSTEM

BACKGROUND

Field

The present disclosure relates to an analyzing apparatus and method, and an image capturing system, and more particularly, to an analyzing apparatus, method, and image capturing system that analyze an image of food in a meal and calculate the ratio of an amount eaten of the food.

Description of the Related Art

In the field of medical care and welfare, the nutritional status of a patient greatly influences the health status of the patient and the cure of the patient's illness. For example, a health problem called undernutrition has become a problem for elderly patients in the field of medical care and welfare. Undernutrition is a condition in which nutrients such as energy and protein necessary for moving the body and nutrients such as vitamins and minerals necessary for maintaining good health are deficient because food intake amount is reduced. When people get older, they may not be able to eat well and their digestive function may be impaired, so they may not be able to have enough nutrients and water, which can easily make them undernourished. In a situation in which a person is unable to eat satisfactorily due to an injury or illness for a period of time, the person can become undernourished even if the person is not elderly. Under such a situation, it is necessary to pay more attention to an elderly person. Undernutrition can cause symptoms such as cognitive decline, weakened immune system, susceptibility to diseases, and bone loss. Mortality is of concern due to weight loss caused by undernutrition.

In order to prevent undernutrition, maintain health, and help recovery from illness and injury, meal management for inpatients in hospitals and residents in nursing facilities has become essential. Presently, meal management for inpatients and residents is performed such that nursing staffs check food in a served meal and the left overs for each patient, record the percentage of the food eaten by each patient on a paper sheet, and then input the percentage into an electronic system storing medical records. In hospitals and nursing facilities, nutrients when food in a meal is completely eaten (called whole meal nutrition data) are managed by registered dietitians. By comparing the percentage of the food eaten by the patient that has been recorded by the nursing staff with the whole meal nutrition data, the amount of food or nutrients ingested by the patient is acquired and managed. The amount of food or nutrients taken by each patient is regularly acquired and is utilized for predicting, preventing, and detecting health disorders based on changes in nutrients and calories.

Currently, since meal management is performed by manually determining and recording the percentage of the remaining amount of food, it takes time to determine and enter the remaining amount of food in the patient's medical record, and the accuracy of the determination on the amount eaten of food can vary between staff members.

Japanese Patent Laid-Open No. 2008-204105 discloses an automatic food intake measuring system that automatically measures food intake. This automatic food intake measuring system measures food intake by comparing an amount of each food detected by a food extraction means from an image of a meal tray before the meal is eaten and an amount of each food detected from an image of the meal tray after the meal is eaten.

Japanese Patent Laid-Open No. 2005-250885 discloses a food and drink intake state management system including a pattern irradiation apparatus, such as a liquid crystal projector and an imaging device, for capturing a three-dimensional image. This food and drink intake state management system is capable of determining the shapes of dishware included in a photographed three-dimensional image using pre-registered information of shapes of dishware and calculating the remaining amounts of food and drink. By comparing the information obtained from images captured before and after eating and drinking, it is possible to detect the types and amounts eaten of the food and drink for each individual.

In the technique disclosed in Japanese Patent Laid-Open No. 2008-204105, in order to perform the three-dimensional measurement in consideration of the depth direction so as to measure the amount eaten more accurately, it is necessary to shoot images from multiple directions. Therefore, there is a drawback that the device configuration becomes complicated in a case where a plurality of image sensors are used to shoot images from multiple directions. In a case of shooting images from multiple directions with a single image sensor, there is a drawback that it takes time to shoot images.

In the technique disclosed in Japanese Patent Laid-Open No. 2005-250885, a pattern irradiation apparatus must be used. In addition, there is a drawback that an optical arrangement in which the angles of inclination of the imaging device and the irradiation apparatus are controlled is required, which makes the configuration complicated. Therefore, as disclosed in Japanese Patent Laid-Open No. 2005-250885, meals must be set on a fixed system such as a checkout table, and it is difficult to take a picture with a hand-held camera.

SUMMARY OF THE INVENTION

The present disclosure estimates a food intake amount from still images of a meal tray with higher accuracy using a system with a simpler configuration than the above-described configuration.

According to the present disclosure an analyzing apparatus comprises a memory storing instructions, and a processor that executes the instructions that configure the processor to: extract, from a food image acquired by an image capturing unit, food information relating to types and served states of foods included in the food image and an edible portion of each food included in the food image, calculate an area ratio between the edible portion of a same type of food extracted from a plurality of food images acquired at different timings, store conversion information for converting the area ratio into a volume ratio corresponding to each type and served state of food, and convert the area ratio of each food into a volume ratio using the conversion information corresponding to the food whose area ratio is to be converted from among the stored conversion information based on the food information.

According to the present disclosure an image capturing system comprises an image capturing apparatus and an analyzing apparatus, wherein the analyzing apparatus comprises a memory, and a processor configured to execute instructions stored in the memory to: extract, from a food image acquired by an image capturing unit, food information relating to types and served states of foods included in the food image and an edible portion of each food included in the food image, calculate an area ratio between the edible portion of a same type of food extracted from a plurality of food images acquired at different timings, store conversion information for converting the area ratio into a volume ratio corresponding to each type and served state of food, and convert the area ratio of each food into a volume ratio using the conversion information corresponding to the food whose area ratio is to be converted from among the stored conversion information based on the food information.

According to the present disclosure an analyzing method comprises extracting, from a food image acquired by an image capturing unit, food information relating to types and served states of foods included in the food image and an edible portion of each food included in the food image, calculating an area ratio between the edible portion of a same kind of food extracted from a plurality of food images acquired at different timings, storing conversion information for converting the area ratio into a volume ratio corresponding to each type and served state of food, and converting the area ratio of each food into a volume ratio using the stored conversion information corresponding to the food whose area ratio is to be converted from among the stored conversion information based on the food information.

According to the present disclosure a non-transitory computer-readable storage medium storing a program that is executable by a computer, which causes the computer to execute a method, the method comprising extracting, from a food image acquired by an image capturing unit, food information relating to types and served states of foods included in the food image and an edible portion of each food included in the food image, calculating an area ratio between the edible portion of a same kind of food extracted from a plurality of food images acquired at different timings, storing conversion information for converting the area ratio into a volume ratio corresponding to each type and served state of food, and converting the area ratio of each food into a volume ratio using the stored conversion information corresponding to the food whose area ratio is to be converted from among the stored conversion information based on the food information.

Further features will become apparent from the following description of exemplary embodiments with reference to the attached drawings.

BRIEF DESCRIPTION OF THE DRAWINGS

The accompanying drawings, which are incorporated in and constitute a part of the specification, illustrate exemplary embodiments, and together with the description, serve to explain the principles of the disclosure.

FIG. 4 is a block diagram illustrating a schematic configuration of an image capturing apparatus according to the first embodiment.

FIG. 5 is a flowchart illustrating an operation of the image capturing apparatus according to the first embodiment.

FIGS. 7A and 7B are views illustrating a guidance screen according to the first embodiment.

FIGS. 9A and 9B are diagrams illustrating region division confirmation screens according to the first embodiment.

FIGS. 10A and 10B are a diagram illustrating an example of a meal management database and a table according to the first embodiment.

DESCRIPTION OF THE EMBODIMENTS

Figure 1:
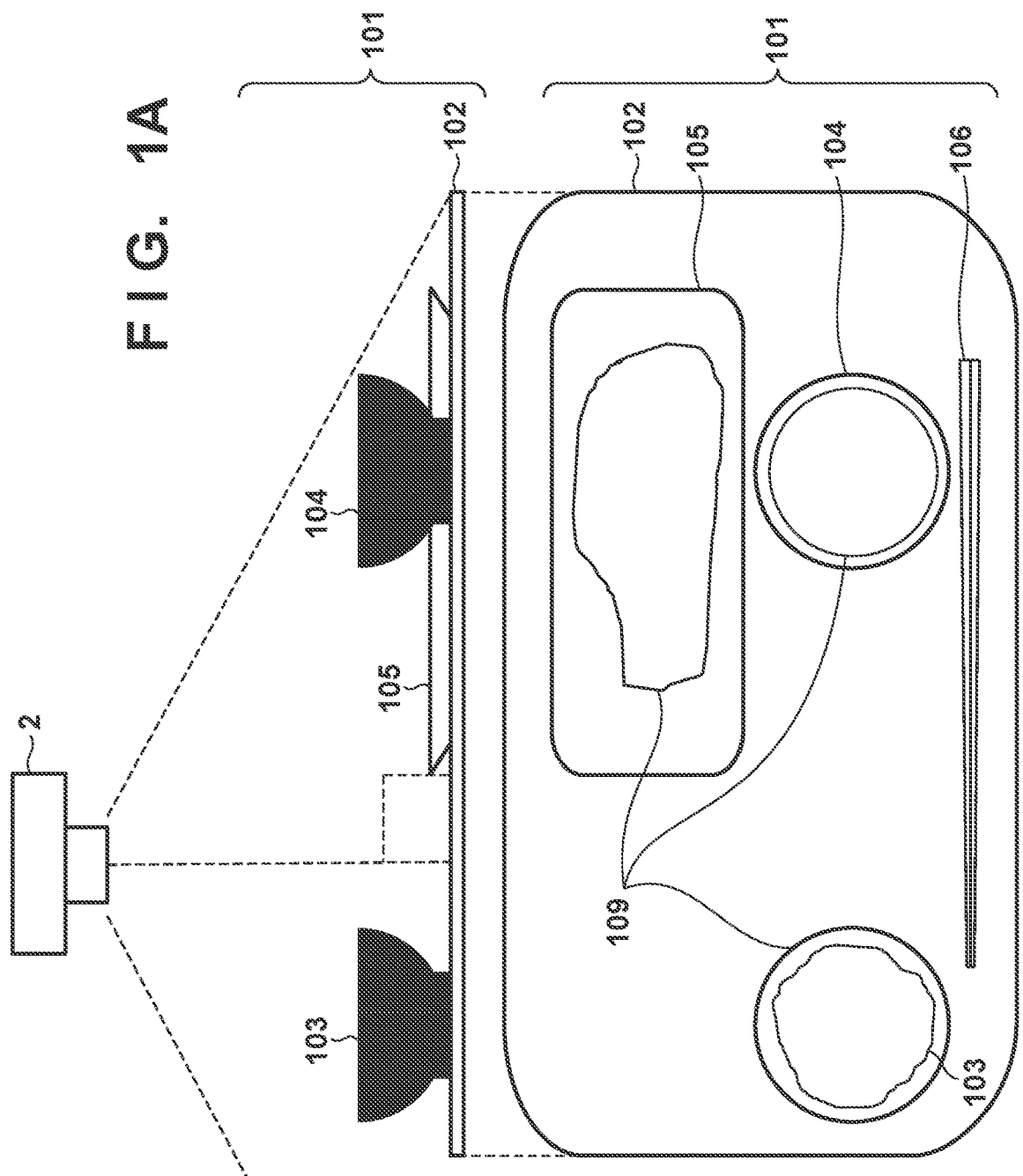
FIGS. 1A and 1B are diagrams illustrating an example of a subject measured by an image capturing system according to a first embodiment.

Hereinafter, embodiments will be described in detail with reference to the attached drawings. The following embodiments are not intended to be limiting. A combination of all features described in the embodiments is not required. Two or more of multiple features described in the embodiments can be combined as appropriate. The same reference numerals are provided to the same or similar configurations, and redundant description thereof is omitted.

FIGS. 1A and 1B are diagrams illustrating an image capturing apparatus 2 and a subject 101 to be shot by the image capturing apparatus 2 according to a first exemplary embodiment. The subject 101 and the image capturing apparatus 2 are arranged to roughly face each other. FIG. 1A illustrates a side view of the subject 101 and FIG. 1B illustrates a top view of the subject 101.

The subject 101 is composed of a meal tray 102, each food placed on the meal tray 102, and a meal tag 107. In the present embodiment, the food in the subject 101 are rice 103, miso soup 104, and pork cutlet 105 placed in bowls and on a dish. In FIG. 1B when the subject 101 is viewed from above, chopsticks 106 are placed on the meal tray 102, and an edible portion 109 of food that does not include the bowls and dish is illustrated.

The meal tag 107 is a form on which a patient's information and instructions regarding meals are written to manage the therapeutic diet of the patient. The meal tag 107 contains information about the patient and meals, such as name, sex, age, menu, date, and breakfast/lunch/dinner. The meal tag 107 can include a barcode, where information printed on the meal tag can be read from the barcode. While the presents embodiment includes a barcode printed on the meal tag 107, the barcode is not always necessary.

The meal tag 107 enables preparing a meal that is prepared according to a patient's condition and provided to an appropriate patient without a mistake occurring. Meal tags also enable helping patients understand what type of meals are provided and the importance of nutritional management. The importance of meal tags is widely recognized, and they are widely used in hospitals and nursing facilities. The present embodiment does not require shooting the meal tag together with the food tray.

The food contained in the subject 101 is not limited to rice 103, miso soup 104, and pork cutlet 105, and various other foods can be considered. The image of the subject 101 can be an object in electronic data, or the subject 101 can be an object located on paper. In such a case, the image of the meal before it is eaten can be reused.

Figure 2:
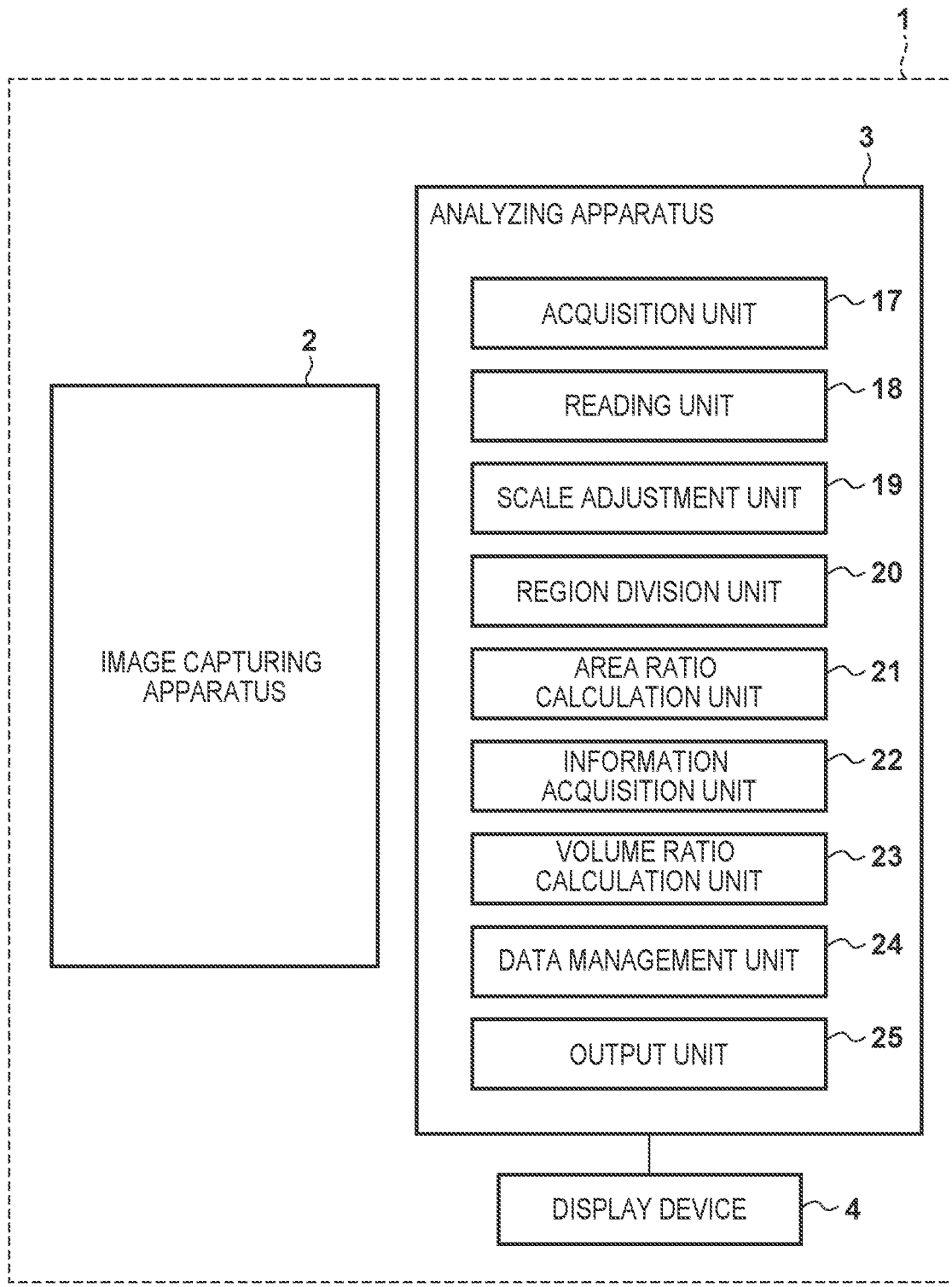
FIG. 2 is a block diagram illustrating a configuration of the image capturing system according to the first embodiment.

FIG. 2 is a block diagram illustrating an example of the configuration of an image capturing system 1 according to the present embodiment. The image capturing system 1 includes the image capturing apparatus 2, which is a hand-held portable device, an analyzing apparatus 3, and a display device 4.

In the image capturing system 1 according to the present embodiment, the image capturing apparatus 2 shoots an image of the subject 101 including the meal tag 107, and the analyzing apparatus 3 recognizes an image of the meal tag 107 from the image of the subject, thereby identifying a user. In the present embodiment, a user refers to, for example, patients at hospitals and residents at nursing facilities.

The image capturing apparatus 2 sends the image data obtained by acquiring images of the subject 101 before and after the meal is eaten to the analyzing apparatus 3, and the analyzing apparatus 3 analyzes the image data, thereby acquiring the ratio of the amount of food after the meal is eaten to the amount of food before the meal is eaten The functional configuration of the analyzing apparatus 3 will now be described. The analyzing apparatus 3 includes an acquisition unit 17, a reading unit 18, a scale adjustment unit 19, a region division unit 20, an area ratio calculation unit 21, an information acquisition unit 22, a volume ratio calculation unit 23, a data management unit 24, and an output unit 25.

The acquisition unit 17 acquires image data and the like from the image capturing apparatus 2. The reading unit 18 reads information about the user and meal, such as name, sex, age, menu, date, and breakfast/lunch/dinner from the image of meal tag 107. The scale adjustment unit 19 matches the sizes of the images of the meal tray 102 acquired before and after the meal is eaten. The region division unit 20 extracts the type of food and the edible portion 109 from the image of the meal trays 102 as illustrated in FIGS. 1A and 1B and divides the region.

The area ratio calculation unit 21 calculates, for each food in the meal tray 102, the type of food and the ratio of the edible portion 109 of the meal tray 102 after the meal is eaten to the edible portion 109 of the meal tray 102 before the meal is eaten as a food area ratio. The information acquisition unit 22 acquires information prepared in advance for each food, food ingredient, dish, or dishware in order to convert the food area ratio calculated by the area ratio calculation unit 21 into a volume ratio. The volume ratio calculation unit 23 converts the food area ratio calculated by the area ratio calculation unit 21 into the volume ratio based on information prepared in advance for each food, food ingredient, dish, or dishware. Thus, for each food in the meal, the ratio of the volume of food after the meal is eaten to the volume of food before the meal is eaten is calculated as the food volume ratio.

The data management unit 24 functions as a database for managing user information, meal information, menu information, initial food amount information, dishware information, and remaining food amount information.

The output unit 25 outputs the information stored by the data management unit 24. Specifically, the information about an analysis result of the meal including the information illustrating the extraction result of the food and the ratio of the amount of food after the meal is eaten to the amount food before the meal is eaten is output. The display device 4 displays the information output from the output unit 25.

Figure 3:
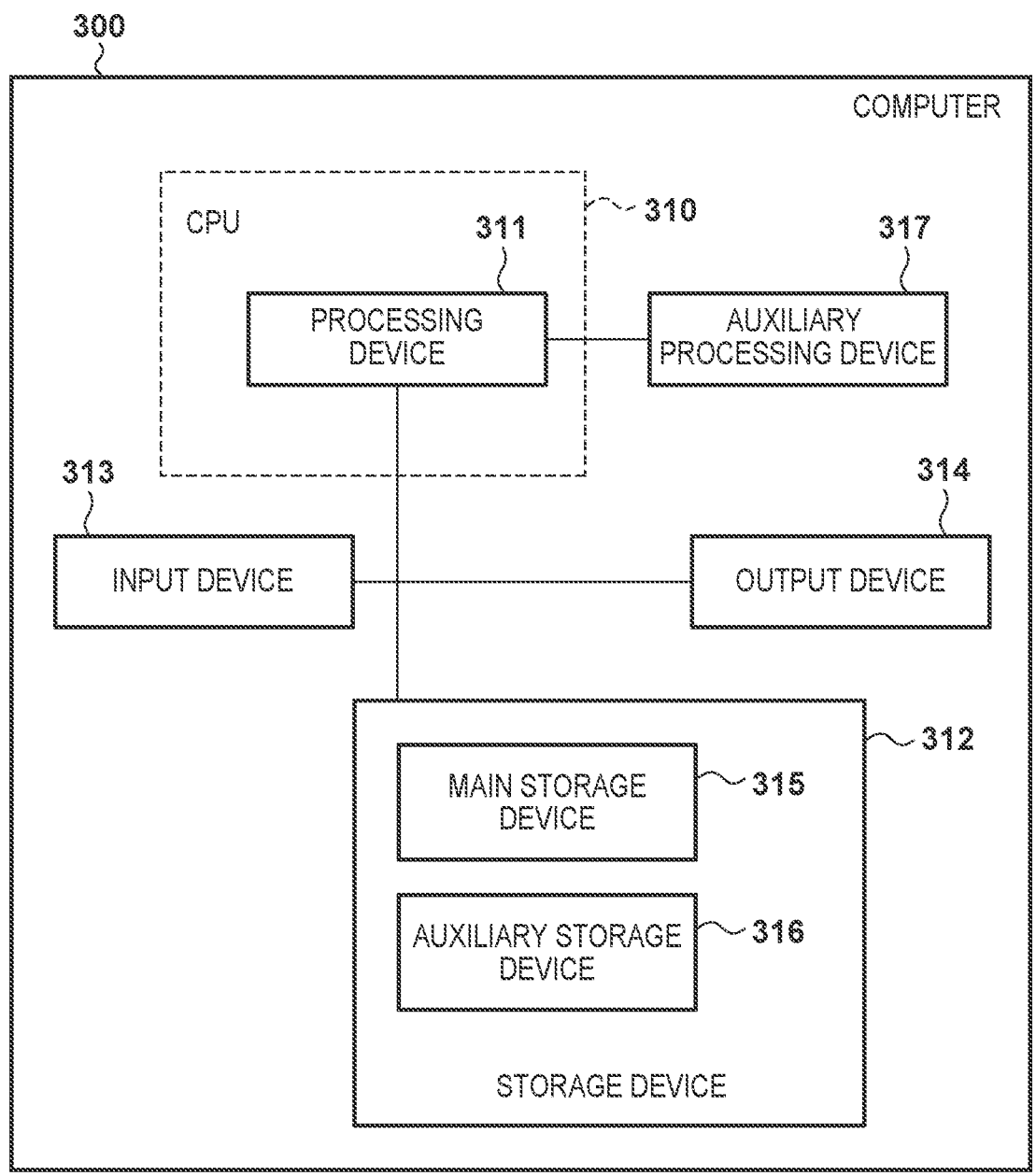
FIG. 3 is a block diagram illustrating an example of a hardware configuration of an analyzing apparatus according to the first embodiment.

As an example of the hardware configuration of the analyzing apparatus 3, FIG. 3 illustrates the configuration of a computer 300. The computer 300 includes a central processing unit (CPU) 310, a storage device 312, an input device 313 such as a mouse and a keyboard, an output device 314 such as a display, and an auxiliary processing device 317. The CPU 310 includes a processing device 311. The storage device 312 includes a main storage device 315 (for example, ROM, RAM, etc.) and an auxiliary storage device 316 (for example, magnetic disk device, solid state drive (SSD), etc.). A part of the input device 313 and the output device 314 is configured as a wireless communication module for performing communication using Wi-Fi®.

The auxiliary processing device 317 is an auxiliary processing IC used under the control of the CPU 310. As the auxiliary processing device 317, a graphic processing unit (GPU) can be used as an example. The GPU is originally a processor for image processing, but since it has a plurality of product-sum operators and is good at matrix calculation, it is often used as a processor for performing deep learning processing. A field-programmable gate array (FPGA), ASIC, or the like can be used as the auxiliary processing device 317.

The processing device 311 included in the CPU 310 functions as each component of the analyzing apparatus 3 illustrated in FIG. 2 by executing programs stored in the storage device 312. That is, the processing device 311 functions as the acquisition unit 17, reading unit 18, scale adjustment unit 19, region division unit 20, area ratio calculation unit 21, information acquisition unit 22, volume ratio calculation unit 23, data management unit 24, and output unit 25. The processing device 311 controls the order in which the above functions are executed.

Computer 300 can include one or more of the CPUs 310 and the storage devices 312. That is, when at least one processing device (CPU) and at least one storage device are connected and at least one processing device executes a program stored in at least one storage device, the computer 300 functions as each unit of the analyzing apparatus 3 illustrated in FIGS. 1A and 1B. The processing device is not limited to being a CPU, and can be an FPGA, an ASIC, or the like.

A schematic configuration of the image capturing apparatus 2 will now be described with reference to FIG. 4.

In the image capturing apparatus 2, an imaging unit 211 has a lens unit 212, a shutter 213, and an image sensor 214, and the lens unit 212 forms an optical image of a subject on the image sensor 214. The image sensor 214 includes a charge-accumulation type solid-state image sensor such as a CCD or a CMOS device that photoelectrically converts an optical image into an electric signal, and performs photo-electrical conversion on the optical image of the subject formed by the lens unit 212 and generates image data. The lens unit 212 includes a diaphragm for adjusting the exposure amount. The shutter 213 opens and closes its aperture to control the image sensor 214 to be exposed to and shielded from light, thereby controlling the exposure period of the image sensor 214. A mechanical shutter, an electronic shutter, or both can be used as the shutter 213.

An AF controller 225 extracts the high-frequency component of an image signal (video signal), searches for the position of a focus lens included in the lens unit 212 that maximizes the high-frequency component, and controls the focus lens to the searched position, thereby focus is adjusted automatically. This focus control method is called TV-AF or contrast AF, and is characterized by being able to focus with high accuracy. The AF controller 225 can also acquire the distance to the subject based on the focus adjustment amount or the position of the focus lens. The focus control method is not limited to the contrast AF, and phase difference AF and other AF methods can be used.

A zoom controller 215 controls driving of a zoom lens included in the lens unit 212. The zoom controller 215 drives the zoom lens via a zoom motor (not shown) based on an instruction from a system controller 219 to perform zooming.

An image processor 217 performs various image processes such as white balance adjustment, gamma correction, color interpolation or demosaicing, filtering, etc. on RAW image data output from the imaging unit 211 or the image data recorded in a storage unit 220 described below. In addition, image processor 217 performs compression processing on the image data captured by the imaging unit 211 based on a standard such as JPEG.

A communication unit 218 is a communication interface for each component of the image capturing apparatus 2 to communicate with an external device such as the analyzing apparatus 3 via a wireless network (not shown). As a specific example of the network, there is a network based on the Wi-Fi® standard. Communication using Wi-Fi® can be realized via a router. Alternatively, the communication unit 218 can be realized by using a wired communication interface such as USB or LAN.

The system controller 219 has a central processing unit (CPU), and performs overall control by controlling each unit of the image capturing apparatus 2 according to a program stored in the storage unit 220.

The storage unit 220 temporarily stores various setting information such as focus position information at the time of image shooting necessary for the operation of the image capturing apparatus 2, RAW image data output from the imaging unit 211, and image data processed by the image processor 217, and so forth. The storage unit 220 can temporarily store image data and the analysis data such as information regarding the size of the subject received by the communication unit 218 via communication with the analyzing apparatus 3. The storage unit 220 can be a rewritable non-volatile memory such as a flash memory and SDRAM.

An external memory 221 is a non-volatile storage medium that is detachably attached to the image capturing apparatus 2 or located internal to the image capturing apparatus 2, and is, for example, an SD card or a CF card. The external memory 221 records image data processed by the image processor 217, image data and analysis data received by the communication unit 218 via communication with the analyzing apparatus 3. During playback, it is possible to read the recorded image data and output it to the outside of the image capturing apparatus 2.

A display unit 222 is used to display image data temporarily stored in the storage unit 220, images and data stored in the external memory 221 and a setting screen of the image capturing apparatus 2. The display unit 222 is a thin film transistor (TFT) liquid crystal, an organic EL display, an electronic viewfinder (EVF), or the like.

An operation unit 223 includes, for example, buttons, switches, keys, a mode dial, etc., and a touch panel coupled with the display unit 222 that are provided in the image capturing apparatus 2. Commands for mode setting, shooting operation by a shutter release operation, and so on, by an operator are input to the system controller 219 via the operation unit 223. In association with guidance displayed on the display unit 222, information regarding the analysis result of the meal is input by the operation unit 223.

A common bus 224 is a signal line for transmitting/receiving a signal between respective blocks. The AF controller 225, imaging unit 211, zoom controller 215, image processor 217, communication unit 218, system controller 219, storage unit 220, external memory 221, display unit 222, and operation unit 223 are connected to the common bus 224.

Figure 6A:
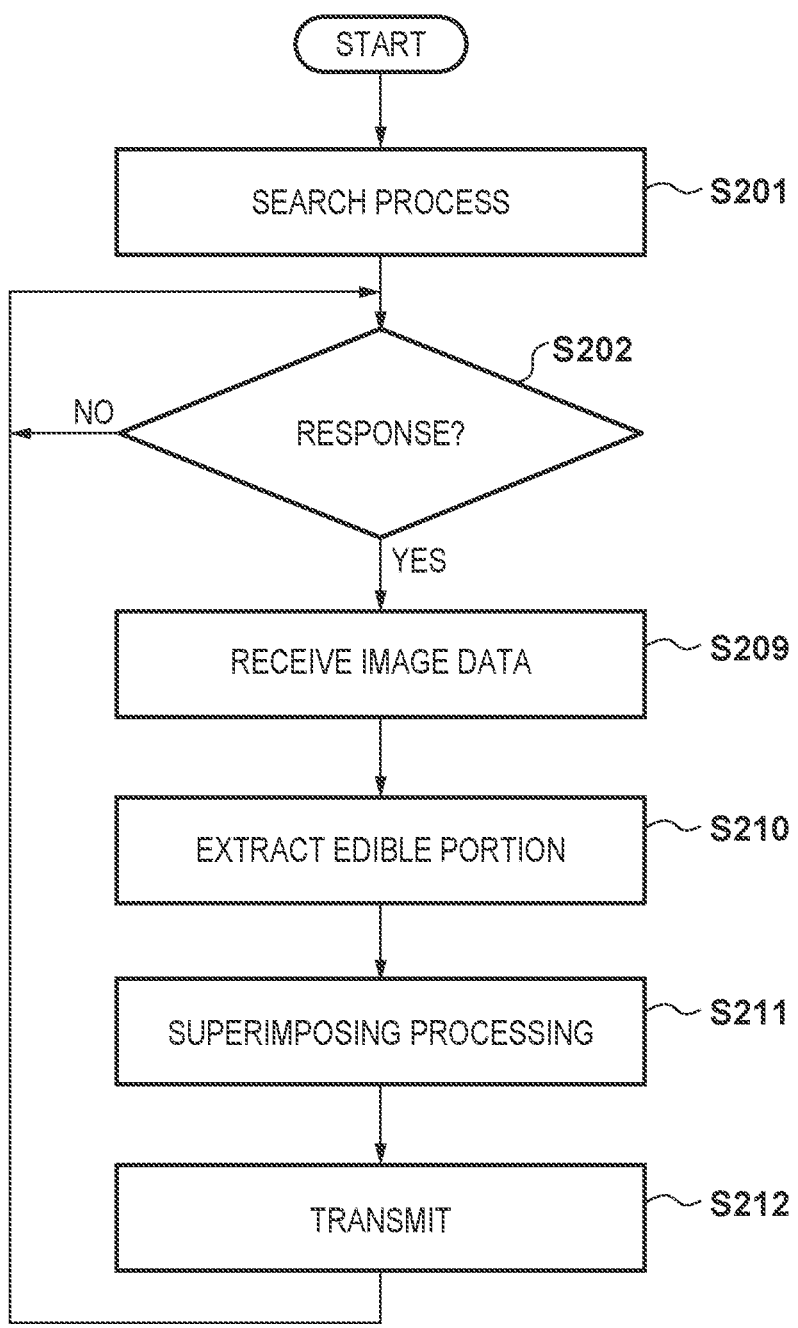
FIGS. 6A and 6B are flowcharts illustrating an operation of the analyzing apparatus according to the first embodiment.
Figure 6B:
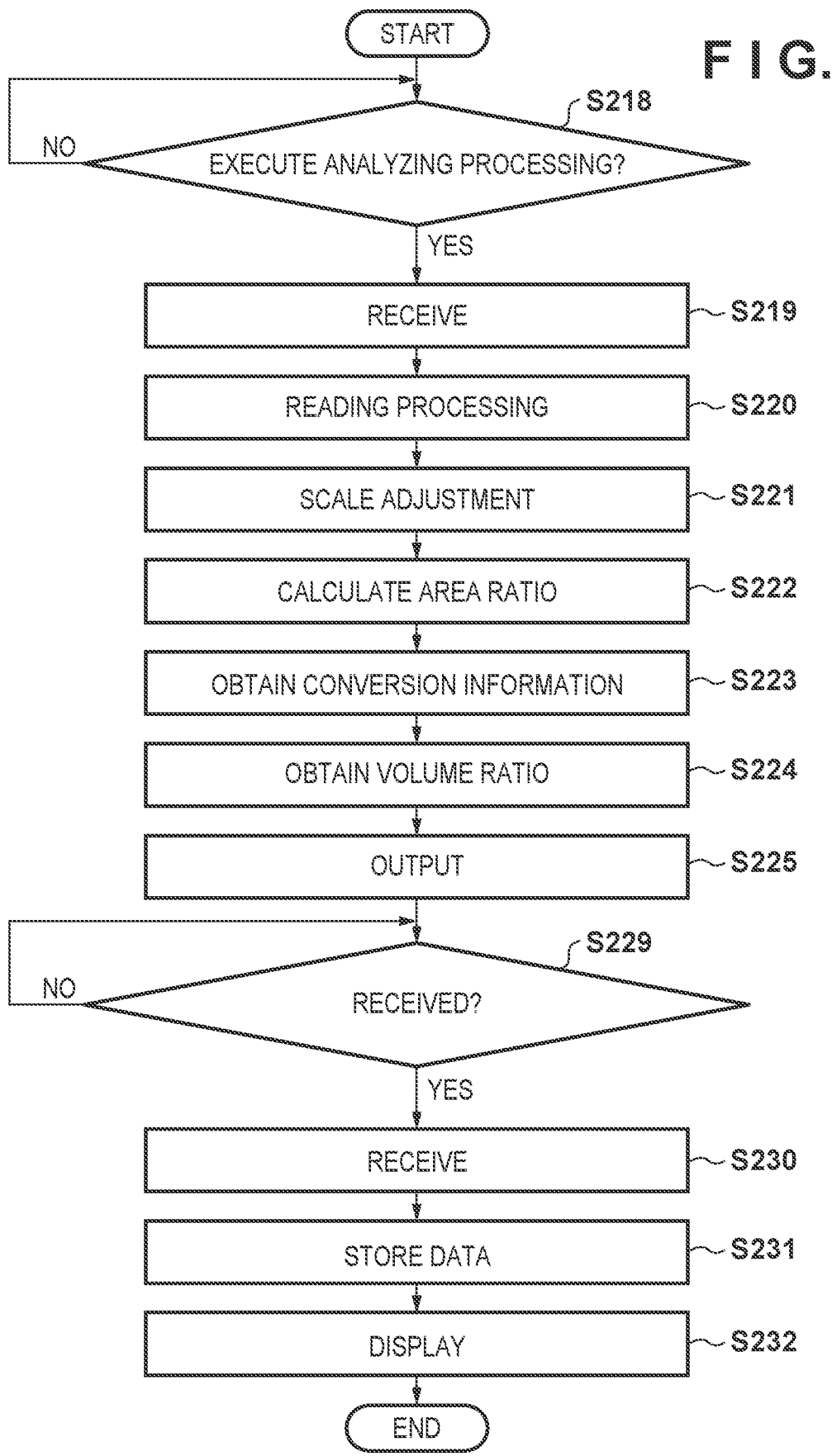

The operation of the image capturing system 1 according to the current embodiment will be described using the flowcharts illustrated in FIGS. 5, 6A and 6B. FIG. 5 illustrates the processing in the image capturing apparatus 2, and FIGS. 6A and 6B illustrate the processing in the analyzing apparatus 3.

First, the image capturing apparatus 2 and the analyzing apparatus 3 are respectively connected to a network of the Wi-Fi® standard (not shown) that is a wireless LAN standard. In step S101, the image capturing apparatus 2 waits for a connection request from the analyzing apparatus 3, and when the connection request is received, the image capturing apparatus 2 performs a response process with respect to the connection request in step S102 and connects to the analyzing apparatus 3. Universal plug and play (UPnP), for example, is used as a technique for searching for a device via a network. In UPnP, each device is identified by a universally unique identifier (UUID).

After connecting to the analyzing apparatus 3, the system controller 219 initializes a variable N that controls the number of repetitions of shooting operation to zero in step S103.

Next, in step S104, image shooting guidance is displayed on the display unit 222. The image shooting guidance differs depending on the value of the variable N that controls the number of repetitions of shooting operation. In the present embodiment, since the subject 101 is shot before and after the meal is eaten, the number of repetitions of shooting operation is two.

Figure 7A:
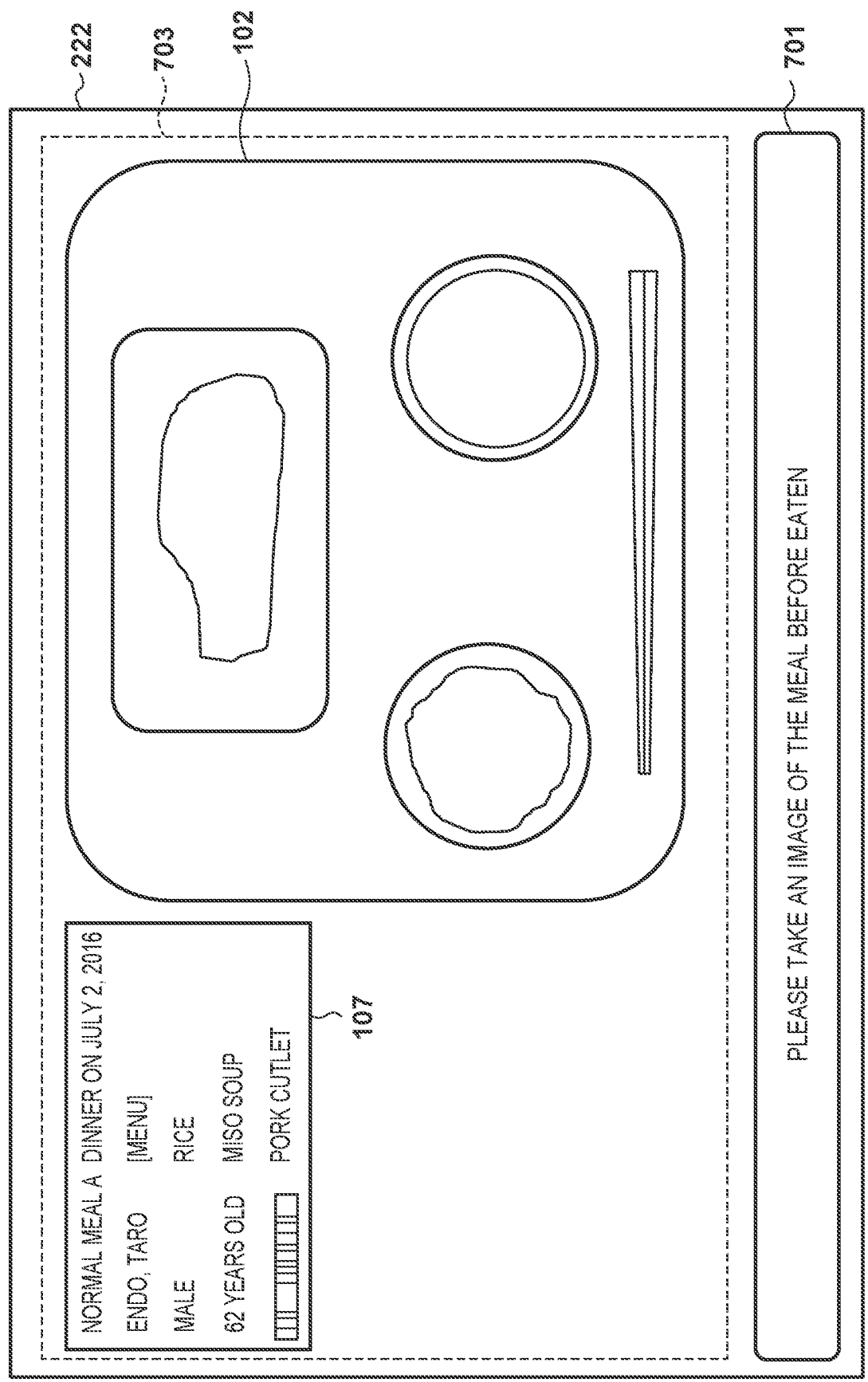

FIGS. 7A and 7B are diagrams illustrating an example of the image shooting guidance displayed on the display unit 222. FIG. 7A is a diagram illustrating a display example when the variable N=0, that is, before the meal is eaten, and a live view image of the meal tray 102 and the meal tag 107, and a guidance 701 ("Please take an image of the meal before eaten") are displayed. FIG. 7B is a diagram illustrating a display example when the variable N=1, that is, after the meal is eaten, and a live view image of the meal tray 102 and the meal tag 107, and a guidance 702 ("Please take an image of the meal after eaten") are displayed. A broken-line is a position guide 703 so that an image of the meal can be acquired at an appropriate position within the frame.

Next, in step S105, image shooting preparation is performed. The AF controller 225 drives the focus lens included in the lens unit 212 to perform AF processing for focusing on the subject 101. In this AF processing, the screen is divided into a plurality of blocks and a predetermined block is focused. In the present embodiment, the user arranges the image capturing apparatus 2 and the subject 101 to face each other, and controls the angle of view such that the subject 101 including the meal tray 102 and the meal tag 107 fits within the screen. At this time, the distance between the subject 101 and the image capturing apparatus 2 can be changed, or the focal length can be adjusted by the zoom controller 215. Both the distance and the focal length can also be adjusted. The aperture value is set so that the food and the whole dishware in the meal tray 102 are in the depth of focus so as to be generally in focus. The exposure value is controlled so that the subject 101 will be shot with appropriate brightness.

In step S106, image shooting operation of the subject 101 is executed by the imaging unit 211 under the shooting conditions set in step S105, and a food image is acquired.

In the image processing in step S107, the image processor 217 develops the food image captured in step S106, generates a bitmap image, resizes the obtained bitmap image, and performs image compression based on a standard such as JPEG. The image data of the compressed food image is transmitted to the analyzing apparatus 3 via wireless communication in step S108. In step S108, the larger the size of the image to be transmitted is, the longer the wireless communication takes. An operator can increase the transmission the time by re-sizing the image size. Since the image size depends on the extraction processing time and the extraction accuracy in the analyzing apparatus 3 described below, the operator selects the image size in consideration of these factors.

In step S108, the image data generated in step S107 is transmitted to the analyzing apparatus 3 via the communication unit 218. The analyzing apparatus 3 analyzes the transmitted image and transmits the result of the analysis to the image capturing apparatus 2.

The processing performed by the analyzing apparatus 3 using the image data transmitted in step S108 will be described with reference to FIG. 6A.

Turning to FIG. 6A, in step S201, the analyzing apparatus 3 performs a search process for searching the image capturing apparatus 2 to be connected, and when receiving a response from the image capturing apparatus 2, the analyzing apparatus 3 waits in step S202 until the image data is transmitted from the image capturing apparatus 2. When the image data is transmitted from the image capturing apparatus 2, the acquisition unit 17 acquires the image data output from the image capturing apparatus 2 in step S209.

In step S210, the region division unit 20 recognizes the food in the subject 101 and extracts the edible portion 109 of the food based on the image data acquired in step S209. As a method of extracting the edible portion 109, semantic region segmentation by deep learning is performed. That is, a learning computer (not shown) preliminarily learns a model of the neural network using a plurality of images of actual food of each of a plurality of types of food as training data to generate a learned model. Then, the ingredients of the edible portion 109 of the food is recognized and the area of the edible portion 109 is estimated from the input image based on the generated learned model. As an example of a neural network model, a fully convolutional network (FCN), which is a segmentation model using deep learning, is applied. Here, the deep learning inference is processed by the GPU included in the auxiliary processing device 317, which is good at parallel execution of product-sum operations. The inference process can be executed by FPGA, ASIC, or the like. The region segmentation can be realized by using another deep learning model. The segmentation method is not limited to deep learning, and for example, graph cut, region growth, edge detection, divide and conquer algorithm, or the like can be used.

Figure 8A:
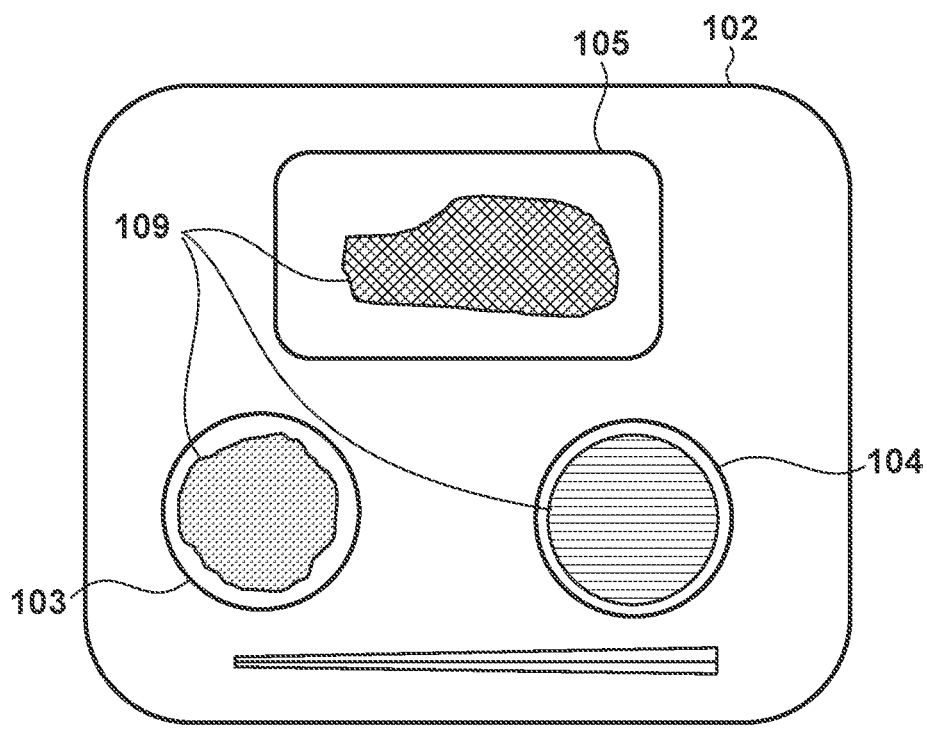
FIG. 8A and FIG. 8B are views explaining superimposing processing according to the first embodiment.
Figure 8B:
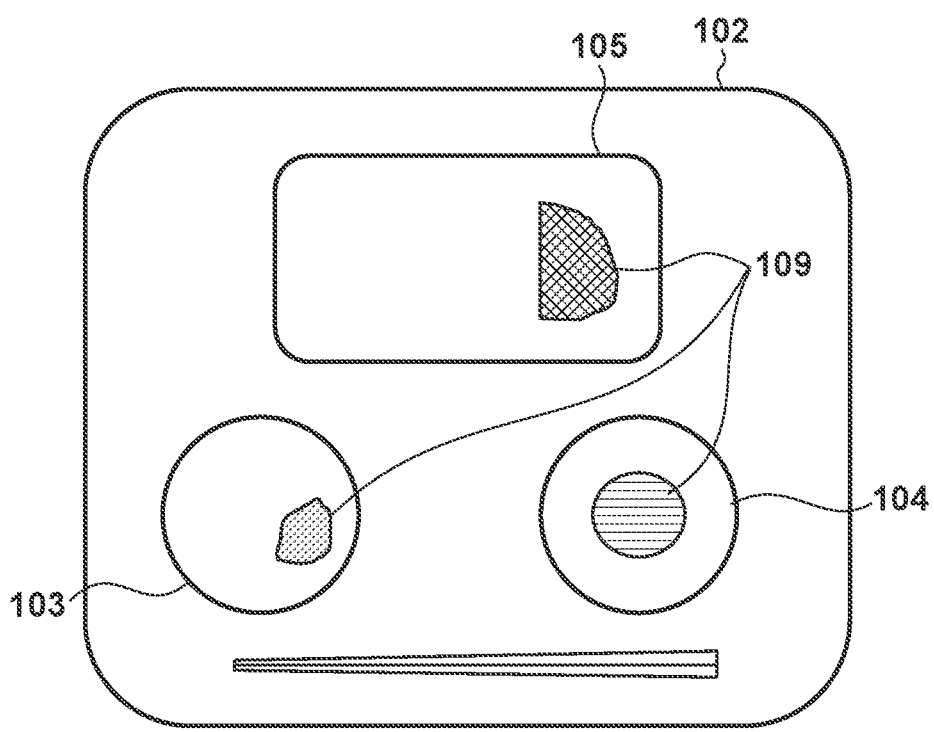

In step S211, the CPU 310 superimposes the result of the edible portion 109 extracted in step S210 on the food image that is based on the acquired image data. FIGS. 8A and 8B illustrate an example of the result of the superimposing processing in step S211. FIG. 8A illustrates an example in which representations illustrating the edible portion 109 of food are superimposed on the image of the meal tray 102 before the meal is eaten. FIG. 8B illustrates representations illustrating the edible portion 109 of food on the image of the meal tray 102 after the meal is eaten. In FIG. 8A and FIG. 8B, a predetermined color or texture set for each type of food is superimposed. In the present embodiment, as examples of patterns to be superimposed, dots are used for the rice 103, horizontal stripes are used for the miso soup 104, and a lattice pattern is used for the pork cutlet 105. In the present embodiment, the patterns to be superimposed are alpha blended, that is, the translucent patterns are superimposed on the original image.

In step S212, the output unit 25 outputs information indicating the extraction result obtained in step S211 to the image capturing apparatus 2. In the present embodiment, the output unit 25 outputs information to the image capturing apparatus 2 via wireless communication. When the output is completed, the process returns to step S202 to wait for the input of the next image data from the image capturing apparatus 2.

Returning to the processing of the image capturing apparatus 2 in FIG. 5, in step S112, the communication unit 218 waits until an image or the information indicating the extraction result of the edible portion 109 of food is input from the analyzing apparatus 3. Then, in step S113, the image that has undergone the superimposing processing and transmitted by the analyzing apparatus 3 in step S212 is obtained. The superimposing processing can be performed by the image capturing apparatus 2 instead of the analyzing apparatus 3.

In step S114, the image that has undergone the superimposing processing and is received in step S113 and a guidance for confirming the extraction result are displayed on the display unit 222. Examples of the region division confirmation screens displayed in step S114 are illustrated in FIGS. 9A and 9B. FIG. 9A illustrates a display example when the variable N=0, that is, before the meal is eaten. FIG. 9B illustrates a display example when the variable N=1, that is, after the meal is eaten. The analysis image of the meal tray 102, a guidance 901 ("Is the meal recognition result correct?"), a choice 902 ("YES"), a choice 903 ("NO"), and the names of food are displayed. Using the operation unit 223, the operator selects the choice 902 "YES" when all the analysis results are correct, and selects the choice 903 "NO" when some of the analysis results are not correct and inputs the choice into the image capturing apparatus 2.

In step S115, when the choice 903 "NO" is selected on the screen illustrated in step S114, the process returns to step S104 to retake an image of the subject 101. When the choice 902 "YES" is selected, the process proceeds to step S116.

In this way, when the choice 902 "YES" is selected, the image is confirmed and the next analysis can be performed. When the choice 903 "NO" is selected, an image can be re-acquired after changing the exposure condition and/or shooting condition such as the position relationship between the meal tray 102 and the image capturing apparatus 2. The UI can be such that the operator can instruct the meal tray 102 to be re-recognized when the image is re-acquired.

By providing the screen for confirming the meal recognition result, it is possible to confirm the validity of the edible portion 109 of the food extracted in step S210 and then use it in the image analysis for the amount eaten of food. When the choice 903 "NO" is selected, instead of retaking an image, the operator can correct the recognized type of food and the edible portion 109 from the image capturing apparatus 2 or the analyzing apparatus 3 by using the operation unit 223 or an operating unit (not shown) of the analyzing apparatus 3. At that time, a menu can be obtained from a database, described below, and the type of food can be selected from the menu illustrated as a pull-down list.

In step S116, the variable N is incremented by 1, and in the following step S117, it is determined whether the variable N is less than 2. That is, when the first shooting operation performed in step S104 to step S115 is completed, the variable N having an initial value of 0 for controlling the repetition number of shootings is incremented to 1 in step S116. Since N=1 satisfies the repetition condition of "N<2" in step S117, the process returns to step S104 and the second shooting operation is performed. When the second shooting operation is completed, the variable N becomes N=2 and the repetition condition N<2 in step S117 is no longer satisfied, and the process proceeds to step S118.

In step S118, a command for instructing execution of analysis processing, the image data generated in step S107, and the correction information of the edible portion 109 if it is input in step S114, are output to the analyzing apparatus 3 via the communication unit 218. Since the image data has been transmitted in step S108, only the command for instructing execution of the analysis processing and the correction information can be transmitted in step S118.

The above processing completes the acquisition of images of the meal before and after the meal is eaten. The analysis processing is then performed in the analyzing apparatus 3 by using the images acquired before and after the meal is eaten and the information of the extraction result of the edible portion 109 as input. The analysis processing performed in the analyzing apparatus 3 using the information transmitted in step S118 will be described with reference to FIG. 6B. Since the analysis processing is performed using a meal management database illustrated in FIGS. 10A and 10B, the meal management database will be described first.

FIGS. 10A and 10B illustrate an example of a table included in the meal management database 1000 that manages information related to the amount of food. The meal management database 1000 is stored in the main storage device 315 via the auxiliary storage device 316 of the analyzing apparatus 3, and writing, reading, and updating of the meal management database 1000 are performed in the processes of steps S220 to S225 described below.

The meal management database 1000 includes a meal table 1001, a user table 1002, a menu table 1003, a food information table 1004, a dish table 1005, a remaining amount information table 1006, and a result table 1007.

The meal table 1001 is a table containing information about one meal of each user, and includes a meal ID as a main key and, as other information, a user ID for identifying the user, a menu ID for identifying a menu, a date, time of meal, classification of meal (breakfast, lunch, dinner).

The user table 1002 is a table including information about each user, and includes a user ID as a main key and, as other information, such as names, sex, age, ward, and room number.

The menu table 1003 is a table containing information about menus, and includes a food information ID, which is a detailed content of food provided in the menus. The menu table 1003 includes a menu ID as a main key and, as other information, a name of the menu, a food information ID corresponding to the main dish, a food information ID corresponding to the side dish 1, and a food information ID corresponding to the side dish 2. The menu table 1003 includes a food information ID corresponding to a soup, a food information ID corresponding to a dessert, and a food information ID corresponding to "other". The food information ID is a main key of a food information table 1004, described below, storing information on the type of food, an amount of food, and dishware. The classification of the main dish and side dishes in the menu table 1003 is not limited to that discussed above, and can be suitably changed for each facility, hospital, etc.

The food information table 1004 is a table containing detailed information on the food used in the menu as described above. The food information table 1004 includes a food information ID as a main key and, as other information, classification indicating the main dish and side dishes of the food, a dish ID identifying a dish that uses this food, and a dishware ID identifying dishware that serves the food. Food information table 1004 includes an initial amount ratio [%] representing a percentage of an amount of food initially served with respect to the standard amount of the food, and a conversion information ID for converting a food area ratio into a volume ratio. The information of the standard amount of the food is included in the dish table 1005 described below.

The dish table 1005 is a table including the name of a dish and information about the nutrients contained in the dish. The dish table 1005 includes a dish ID as a main key and, as other information, a food name, a standard amount of the dish [gram], and amounts of carbohydrate [gram], protein [gram], lipid [gram], vitamins [gram], minerals [gram], and dietary fiber [gram].

The remaining amount information table 1006 is a table including information on the remaining amount and the amount eaten of a meal of the user. The remaining amount information table 1006 includes a remaining amount information ID as a main key and, as other information, a meal ID, a food information ID, a remaining area [%] (hereinafter, referred to as "area ratio") that represents a ratio of the area of the food after the meal is eaten to an initial area of the food provided to the user, a remaining volume [%] that represents a ratio of volume of the same, and an amount eaten [%] of food with respect to the standard amount. The amount eaten [%] with respect to the standard amount is calculated by using an initial amount ratio [%] that is included in the list of the food information table linked to the food information ID of the remaining amount information table 1006 and the remaining volume [%], from the expression of (initial amount ratio [%])×(1−remaining volume [%]).

The result table 1007 illustrates the result of calculating the value of the amount eaten [gram] considering the leftover food based on the contents of the items obtained by combining the tables 1001 to 1006. By taking the product of the standard amount [gram] and the amount eaten [%] with respect to the standard amount, the amount eaten [gram] by the user can be obtained.

The information in the tables 1002, 1003, 1004, and 1005 is assumed to be prepared in advance before a meal time.

The analyzing apparatus 3 waits for the command instructing execution of the analysis processing to be transmitted from the image capturing apparatus 2 in step S218. When the command instructing execution of the analysis processing is received, the process proceeds to step S219, and the analyzing apparatus 3 receives the image data generated by the image processing in step S107 and the correction information input in step S114.

In step S220, the reading unit 18 reads information about the user and meal such as name, sex, age, menu, date, and breakfast/lunch/dinner from the image of the meal tag 107. In the present embodiment, the barcode printed on the meal tag 107 is read. The barcode includes information other than the information printed on the meal tag 107, and information on the user ID, menu ID, date, time, breakfast/lunch/dinner included in the meal table 1001 in the meal management database 1000 illustrated in FIGS. 10A and 10B are input to the main storage device 315 via the auxiliary storage device 316. The information stored in advance in the user table 1002 and the menu table 1003 can be referred to by using the user ID and menu ID as keys.

A QR Code® can be used instead of the barcode. In addition, if the user always has meals at a fixed location, such as in a private room, a tray (meal tray) with an RFID can be used. Reading of a meal tag can be replaced by storing the information corresponding to the meal tag in the RFID, providing an RFID reader at the location where the user has meals, and connecting the RFID reader to the analyzing apparatus 3.

In step S221, the scale adjustment unit 19 performs scale adjustment to match the sizes of the meal tray 102 in the images acquired before and after the meal is eaten.

Figure 11A:
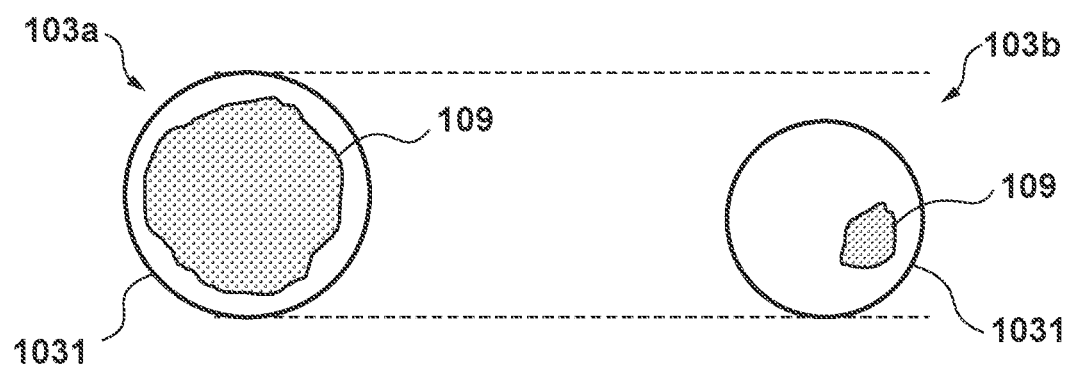
FIGS. 11A and 11B are views illustrating scale adjustment according to the first embodiment.
Figure 11B:
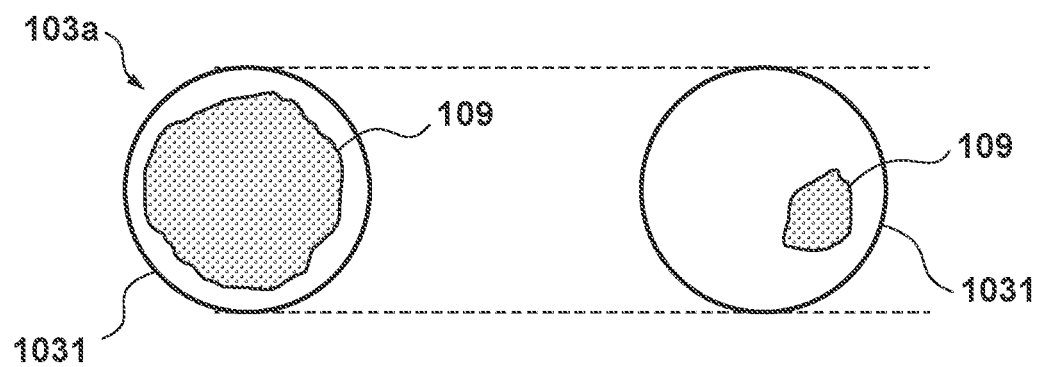

A diagram for explaining the scale adjustment is illustrated in FIGS. 11A and 11B. Images of the meal tray 102 acquired before and after the meal is eaten can have different sizes when the distances between the image capturing apparatus 2 and the food differ between the images. FIG. 11A illustrates a pre-meal image 103a and a post-meal image 103b of the rice 103 before the scale adjustment, each including dishware 1031 and the edible portion 109 of the food. Comparing the pre-meal image 103a with the post-meal image 103b, the size of the dishware 1031 and the area of the food edible portion 109 are both smaller in the post-meal image 103b. In such a case, the dishware is recognized and extracted in the same way as the extraction of food, and the scaling factor is calculated so that images of the dishware acquired before and after the meal is eaten have the same size or area, and enlarge or reduce either of the images. When there are a plurality of pieces of dishware, a plurality of scaling factors can be averaged.

FIG. 11B illustrates the pre-meal image 103a and the post-meal image 103b after the scale adjustment. In this way, the amount eaten of food can be accurately measured by matching the scales of the images of the meal acquired before and after the meal is eaten.

At the time of recognizing the dishware and linking the dishware in the images acquired before and after the meal is eaten, the plurality of pieces of dishware in the meal tray can be ranked based on their sizes such as the length and area of the dishware, and the images can be scaled such that the dishware having the same size ranking has the same size in the images. In this way, even if a piece of the dishware having the same shape is placed at different positions before and after the meal is eaten, it is possible to adjust the scales of the same piece of the dishware.

In step S222, the area ratio calculation unit 21 calculates the ratio of the area of ingredients of food in the image acquired after the meal is eaten to that acquired before the meal is eaten based on the scale-adjusted images processed in step S221. The obtained data is input to the remaining area [%] of the remaining amount information table 1006 in the meal management database 1000 in FIGS. 10A and 10B via the auxiliary storage device 316 of the analyzing apparatus 3.

In step S223, the information acquisition unit 22 acquires conversion information prepared in advance for each food, ingredients of food, dish or dishware in order to convert the food area ratio calculated by the area ratio calculation unit 21 into a volume ratio. In this process, conversion information associated with the conversion information ID for converting each food area ratio into a volume ratio is acquired from the food information table 1004 in the meal management database 1000 in FIGS. 10A and 10B. The conversion information is information to which both the area ratio and the volume ratio correspond.

Figure 12A:
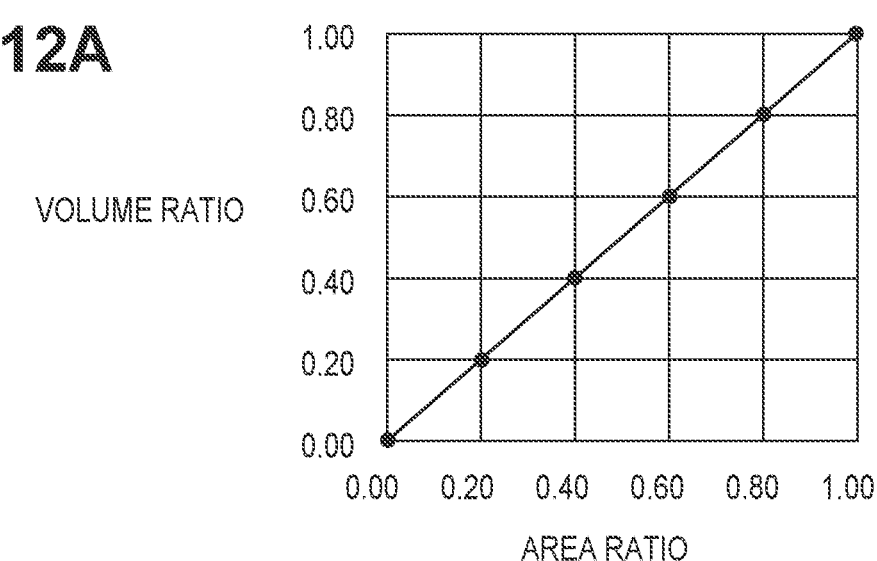
FIGS. 12A and 12B are diagrams illustrating conversion information according to the first embodiment.
Figure 12B:
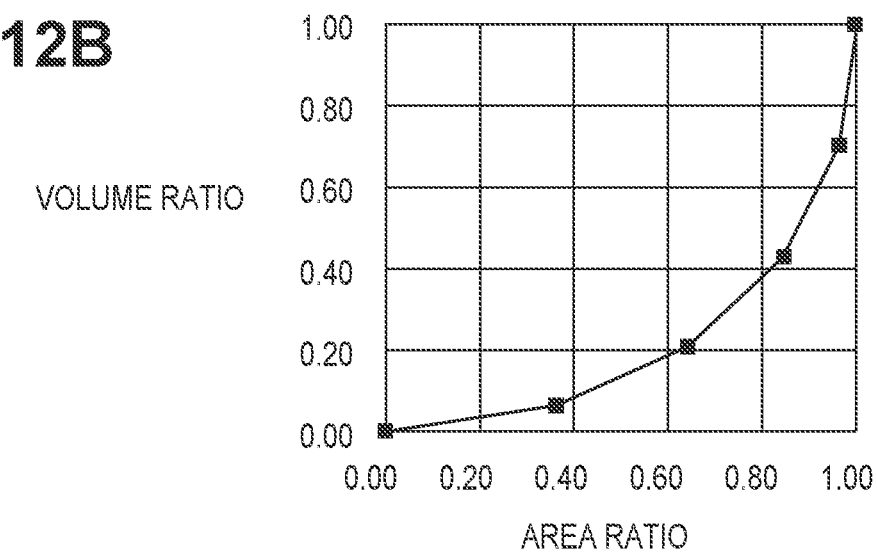

The conversion information will be described with reference to FIGS. 12A and 12B as an example. FIGS. 12A and 12B are graphs illustrating conversion information, wherein the horizontal axis represents the area ratio and the vertical axis represents the volume ratio. FIG. 12A is a graph of conversion information of pork cutlet, and FIG. 12B is a graph of conversion information of miso soup in a bowl. Since the pork cutlet has substantially uniform thickness, the graph of the conversion information of the pork cutlet is a straight line because the ratio of the area of food viewed from above to the volume is proportional. With respect to the miso soup in the bowl, since the relationship between the area and the volume is not proportional, the graph of the conversion information of miso soup is as illustrated in FIG. 12B.

As described above, the conversion information depends on the food, the type of dish, and the initial amount. Therefore, a plurality of pieces of conversion information are prepared in advance in association with the food ID, dishware ID, and initial amount ratio [%] of the food information table 1004 acquired by the information acquisition unit 22, and the information acquisition unit 22 acquires the conversion information by linking to the conversion information ID, and uses the acquired conversion information to convert the area ratio to the volume ratio. The dish ID is an ID that identifies the dish and the nutrient, and the dish and the nutrient can be identified by referring to the dish table 1005 prepared in advance. The conversion information can be obtained by interpolation or can be represented by a function.

Figure 13:
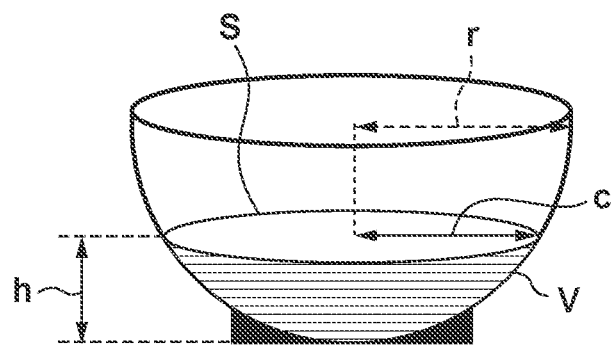
FIG. 13 is a diagram illustrating an example of a conversion information generation method according to the first embodiment.

In generating the conversion information in the present embodiment, a hemispherical bowl is assumed and used for calculation. Specifically, FIG. 13 illustrates an example of a generation method of conversion information. FIG. 13 is a diagram schematically illustrating the contents (soup) in a hemispherical container, where S is the area of the soup seen from above, r is the radius of the bowl, c is the radius of the contents (soup), V is the volume, and h is the height from the bottom of the bowl to the surface of the contents. Then, when the shape of the container is hemispherical and r is known, c can be expressed by the equation (1), and S and V can be expressed by the equation (2) and the equation (3) using the equation (1), respectively.

$$c = \sqrt{(h(2r-h))} \tag{1}$$

$$S = \pi c^2 \tag{2}$$

$$V = (\pi/6) \times h(3c^2 + h^2) \tag{3}$$

The conversion information can be generated by normalizing the area S and the volume V with the initial values obtained from the food information table 1004. If the shape of the container is complicated, it may not be possible to obtain the conversion information by calculation. In such a case, the area and volume can be actually measured by actually putting food in the container to obtain the conversion information. The form of food need not be soup.

There is a case in which, depending on the type of food and container, the food in the initial state has substantially the same area even if the initial amounts of food are different. For example, there is no difference in area between white rice and heaped white rice. In such a case, the conversion information can be determined using deep learning based on the difference in texture of the image instead of the area. The conversion information acquired in step S223 can be prepared for each user in consideration of how the user leaves food.

In step S224, the volume ratio calculation unit 23 calculates the volume ratio from the area ratio using the area ratio calculated in step S222 and the conversion information generated based on the information acquired in step S223. The volume ratio corresponds to the ratio of a remaining amount of uneaten food to the amount of food initially provided to the user, that is, the initial amount, and this data is input to the remaining volume [%] in the remaining amount information table 1006 via the auxiliary storage device 316. By performing this process for each food in the meal tray 102, the ratio of the volume of food after the meal is eaten to the volume of food before the meal is eaten is obtained as a food volume ratio of each of a plurality of foods in the menu for each user.

In step S225, the output unit 25 of the analyzing apparatus 3 outputs information indicating the extraction result of the meal, that is the information stored by the meal management database 1000, and information regarding the analysis result of the meal including the ratio of the amount of food after the meal is eaten to the amount of food before the meal is eaten to the image capturing apparatus 2.

Returning to FIG. 5, after outputting the information in step S118, the image capturing apparatus 2 waits for the information to be transmitted from the analyzing apparatus 3 in step S125. When the above-mentioned information is transmitted from the analyzing apparatus 3, in step S126, the communication unit 218 receives the information output by the output unit 25 of the analyzing apparatus 3 in step S225.

In step S127, the display unit 222 displays the information indicating the extraction result of the meal and information about the analysis result of the meal including the ratio of the amount of food after the meal is eaten to the amount of food before the meal is eaten.

FIGS. 14A to 14D illustrate an example of the display of the information regarding the analysis result of the meal displayed on the display unit 222 of the image capturing apparatus 2. A pre-meal tab 1401, a post-meal tab 1402, and a result tab 1403 are displayed on the display screen of the display unit 222. These tabs can be switched by operating the operation unit 223 of the image capturing apparatus 2.

Figure 14A:
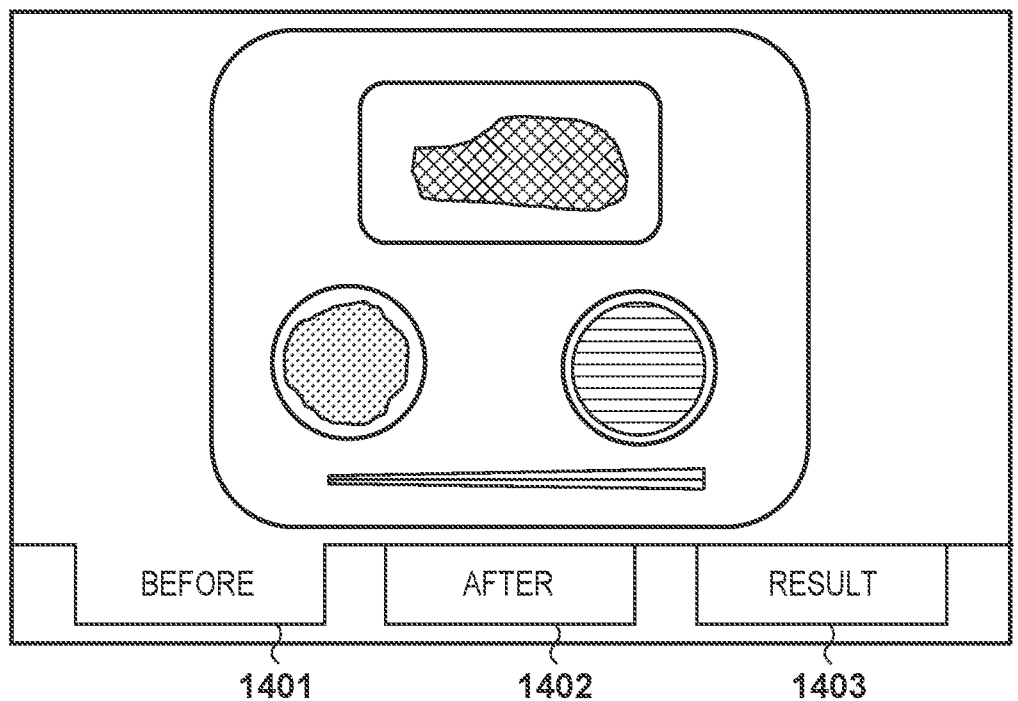
FIG. 14A to FIG. 14D are views illustrating display examples of information related to an analysis result of a meal according to the first embodiment.
Figure 14B:
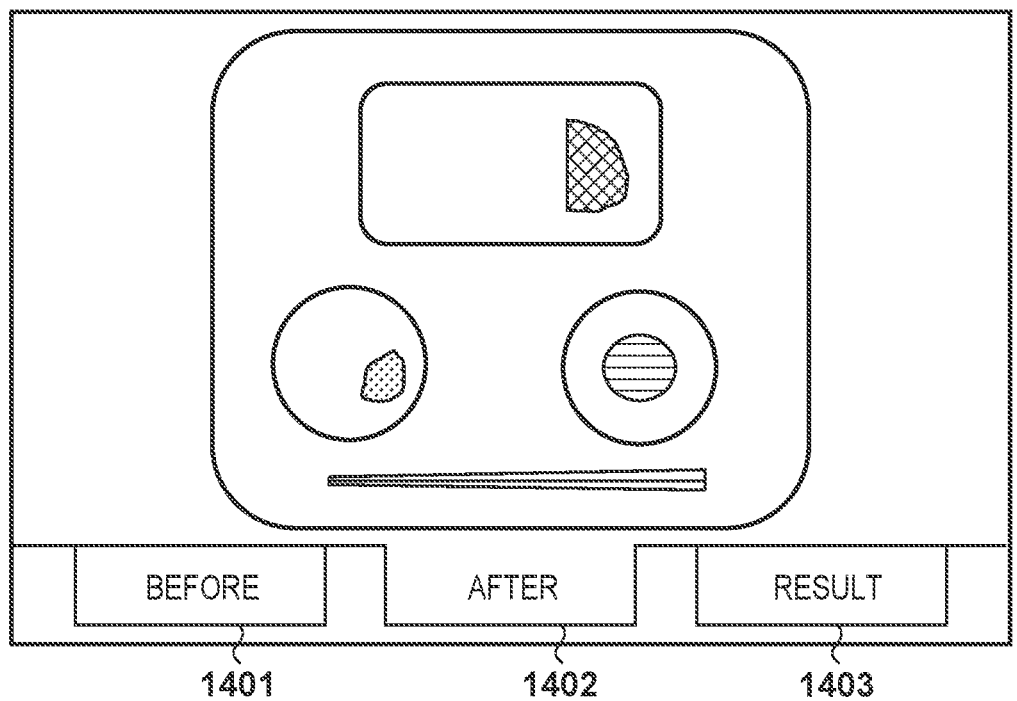
Figure 14C:
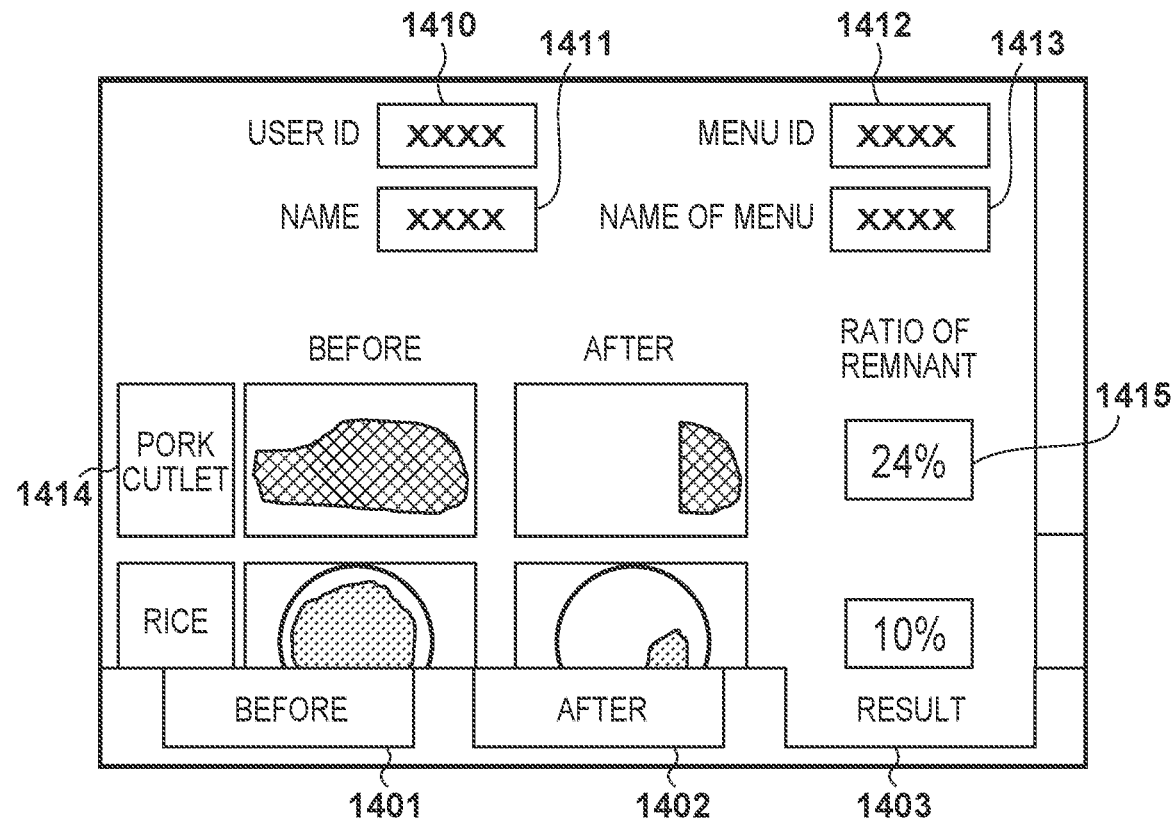
Figure 14D:
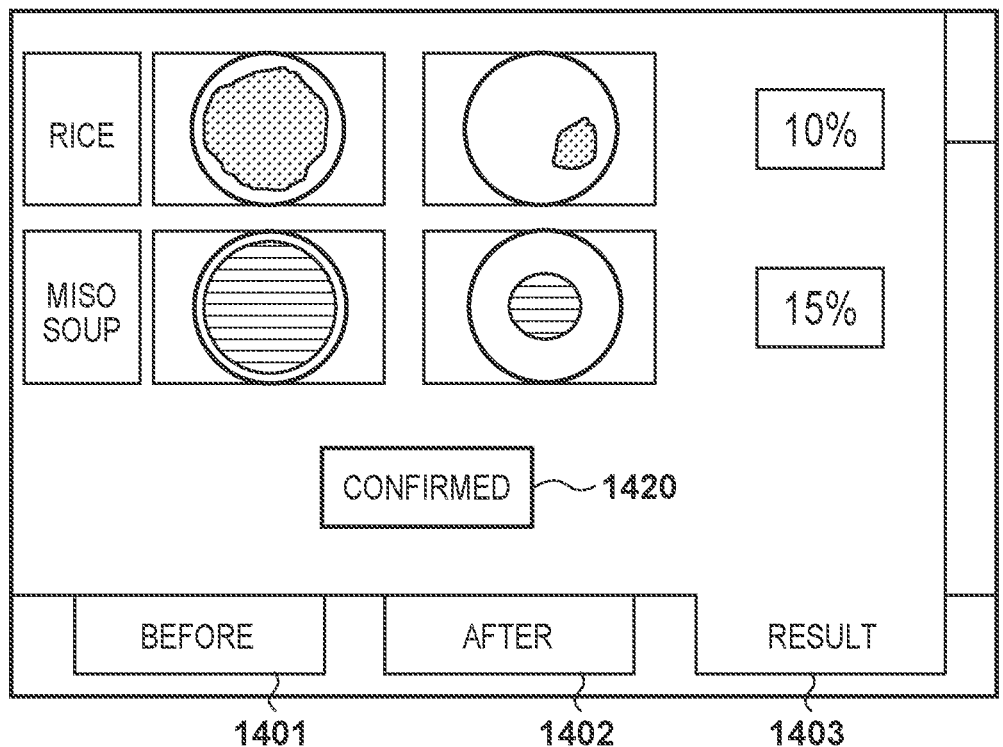

When the pre-meal tab 1401 is selected, an image of the meal tray 102 acquired before the meal is eaten as illustrated in FIG. 14A is displayed. When the post-meal tab 1402 is selected, an image of the meal tray 102 acquired after the meal is eaten is displayed as illustrated in FIG. 14B. When the result tab 1403 is selected, as illustrated in FIG. 14C, a food name 1414 and a remaining ratio 1415 corresponding to the food name 1414 are displayed as the analysis result of the amount eaten of food. The display unit 222 displays a user ID 1410, a user name 1411, a menu ID 1412, and a menu name 1413. By confirming the displayed contents under the result tab 1403, the operator of the image capturing apparatus 2 can confirm whether the analysis result of the meal is appropriate immediately after an image of the meal tray 102 is acquired.

In step S128, the operator inputs information regarding the analysis result of the meal using the operation unit 223 of the image capturing apparatus 2. Specifically, when the operator's recognition is different from the contents displayed in step S127, the operator operates the operation unit 223 to directly input a corrected value/values in all or part of the boxes of the food name 1414, the remaining ratio 1415, the user ID 1410, the user name 1411, the menu ID 1412 and the menu name 1413. The food name can be selected from the food list included in the menu table 1003 of the meal management database 1000. Then, by pressing the "confirmed" button 1420 illustrated in FIG. 14D, the display contents are confirmed. With such a configuration, it is possible to check the user information, menu information, information prepared in advance for each food, each ingredients of food, each dish and/or each dishware, and analysis results and to correct them as necessary.

In step S129, the information regarding the analysis result of the meal input from the operation unit 223 in step S128 is transmitted to the analyzing apparatus 3 via the communication unit 218, and the processing ends.

Returning to FIG. 6B, the analyzing apparatus 3 waits for the information from the image capturing apparatus 2 to be received, and in step S230, the acquisition unit 17 acquires the information about the analysis result of the meal output from the image capturing apparatus 2.

Then, in step S231, the data management unit 24 stores the information acquired and generated in steps S220 to S224 as well as the information regarding the analysis result of the meal received in step S230 in the meal management database 1000 in the main management device 315 via the auxiliary storage device 316. The information can be stored at the timing when each piece of information is acquired or generated. The stored information is organized and accumulated in an easy-to-use state as illustrated in FIGS. 10A and 10B, and utilized. The database can be, for example, a relational database (RDBMS).

In step S232, the display device 4 connected to the analyzing apparatus 3 displays information indicating the extraction result of food and information about the analysis result of the meal including the ratio of the amount of food after the meal is eaten to the amount of food before the meal is eaten. The display on the display unit 222 of the image capturing apparatus 2 in step S126 illustrates the minimum amount of information for the operator of the image capturing apparatus 2 to judge the validity of the analysis result. In step S232, the information necessary for the user's meal management is extracted from the meal management database 1000 and displayed appropriately. For example, the trend of amount eaten of food, calories, and nutrients can be displayed in graphs. Weight, medication information, etc. can be obtained from an information management system in a hospital or facility and displayed together with the information of meal.

As described above, according to the present embodiment, the amount eaten of a meal can be automatically measured by only taking images of a meal tray before and after the meal is eaten with an image capturing apparatus by the operator. It is possible to accurately estimate the proportion of the food that the user has ingested by taking the three-dimensional shapes of food estimated from the still images acquired by the same image capturing apparatus into consideration. As a result, it is possible to record the amount of food and the nutrients ingested by the user with a certain accuracy as compared with a diet management method in which a person judges an amount of food. Further, it is possible to reduce the burden on a staff for recording the amount eaten of food.

In the present image capturing system, the image capturing apparatus 2 and the analyzing apparatus 3, or either of them can be a mobile terminal such as a smartphone or a tablet. The image capturing apparatus 2 and the analyzing apparatus 3 can be integrated as a single apparatus in the present image capturing system.

A second exemplary embodiment will not be described. In the image capturing system 1 according to the first embodiment described above, the analyzing apparatus 3 has the scale adjustment unit 19, and the scales of the images of food acquired before and after the meal is eaten are adjusted by expanding or reducing at least one of the images. In the image capturing system according to the second embodiment, the image capturing apparatus 2 acquires the distance from the image capturing apparatus 2 to the subject, transfers the acquired distance information to the analyzing apparatus 3, and the analyzing apparatus 3 uses this distance information to perform scale adjustment.

Various methods can be used as a method of acquiring distance information, and the present disclosure is not limited to any specific method(s). For example, the distance information can be generated based on an output from the AF controller 225 of the image capturing apparatus 2. A time Of flight (TOF) sensor can be provided and used to generate the distance information. The TOF sensor measures the distance to the object based on the time difference (or phase difference) between the transmission timing of a radiated wave and the reception timing of a reflected wave that is the radiated wave reflected by the subject. A position sensitive device (PSD) method using a PSD as the light receiving element can be used to measure the distance.

If the image capturing apparatus 2 has a zoom function, since the size of the subject in an image changes as the zoom magnification changes, the zoom magnification is output to the analyzing apparatus 3 together with the distance information. Then, the analyzing apparatus 3 perform the scale adjustment in consideration of the zoom magnification.

As described above, according to the present embodiment, by obtaining the distance information, it is possible to more accurately estimate the eaten amount of food from one image based on the distance information, the information about the angle of view of the image capturing apparatus, and the region division result. When the information on the zoom magnification is obtained, it is possible to more accurately estimate the amount eaten of food in consideration of the zoom magnification.

While exemplary embodiments have been described, these embodiments are not seen to be limiting. The scope of the following claims is to be accorded the broadest interpretation so as to encompass all such modifications and equivalent structures and functions.

This application claims the benefit of Japanese Patent Application No. 2019-213650, filed on Nov. 26, 2019 which is hereby incorporated by reference herein in its entirety.

What is claimed is:

1. An analyzing apparatus comprising:
a memory storing instructions; and
a processor that executes the instructions that configure the processor to:
rank a container for serving each food in a plurality of food images acquired by an image capturing unit at different timings;
enlarge or reduce at least any one of the plurality of food images to match the sizes of the container of a same rank in the plurality of food images in order to match the size of each food in the plurality of food images;
extract, from the plurality of food images, food information relating to types and served states of foods included in the food images and an edible portion of each food included in the food images;
calculate an area ratio between the edible portion of a same type of food extracted from the plurality of food images; and
convert the area ratio of each food into a volume ratio using conversion information corresponding to the food whose area ratio is to be converted from among conversion information corresponding to each type and served state of food based on the food information.

2. The analyzing apparatus according to claim 1, wherein the food information relating to the served states of food includes information about ingredients of the food, type of dish the food is, and a container for serving the food.

3. The analyzing apparatus according to claim 2, wherein the processor executes the instructions that further configure the processor to select the type of dish from menu information prepared in advance.

4. An analyzing apparatus comprising:
a memory storing instructions; and
a processor that executes the instructions that configure the processor to:
enlarge or reduce a size of at least any of a plurality of food images acquired by an image capturing unit at different timings to match sizes of each food in the plurality of food images;
extract, from the plurality of food images, food information relating to types and served states of foods included in the food images and an edible portion of each food included in the food images;
calculate an area ratio between the edible portion of a same type of food extracted from the plurality of food images; and
convert the area ratio of each food into a volume ratio using conversion information corresponding to the food whose area ratio is to be converted from among conversion information corresponding to each type and served state of food based on the food information,
wherein the processor uses an average value of magnification values for matching the size of the respective foods included in the plurality of food images to enlarge or reduce at least any one of the plurality of food images.

5. The analyzing apparatus according to claim 1, wherein the processor executes the instructions that further configure the processor to superimpose an indication illustrating the edible portion of each food extracted from the plurality of food images on the food image.

6. The analyzing apparatus according to claim 1, wherein the different timings are a timing before a meal is eaten and a timing after the meal is eaten.

7. The analyzing apparatus according to claim 1, wherein the processor executes the instructions that further configure the processor to read, in a case where an image of a meal tag is included in the food image, information of the meal tag.

8. An image capturing system comprising:
an image capturing apparatus; and
an analyzing apparatus,
wherein the analyzing apparatus comprises:
a memory storing instructions; and
a processor that executes the instructions that configure the processor to:
rank a container for serving each food in a plurality of food images acquired by an image capturing unit at different timings;
enlarge or reduce at least any one of the plurality of food images to match the sizes of the container of a same rank in the plurality of food images in order to match the size of each food in the plurality of food images;
extract, from the plurality of food images, food information relating to types and served states of foods included in the food images and an edible portion of each food included in the food images;

calculate an area ratio between the edible portion of a same type of food extracted from the plurality of food images; and convert the area ratio of each food into a volume ratio using conversion information corresponding to the food whose area ratio is to be converted from among conversion information corresponding to each type and served state of food based on the food information.

9. An analyzing method comprising:

ranking a container for serving each food in a plurality of food images acquired by an image capturing unit at different timings;

enlarging or reducing at least any one of the plurality of food images to match the sizes of the container of a same rank in the plurality of food images in order to match the size of each food in the plurality of food images;

extracting, from the plurality of food images, food information relating to types and served states of foods included in the food images and an edible portion of each food included in the food images;

calculating an area ratio between the edible portion of a same kind of food extracted from the plurality of food images; and converting the area ratio of each food into a volume ratio using conversion information corresponding to the food whose area ratio is to be converted from among conversion information corresponding to each type and served state of food based on the food information.

10. A non-transitory computer-readable storage medium storing a program that is executable by a computer, which causes the computer to execute a method, the method comprising:

ranking a container for serving each food in a plurality of food images acquired by an image capturing unit at different timings;

enlarging or reducing at least any one of the plurality of food images to match the sizes of the container of a same rank in the plurality of food images in order to match the size of each food in the plurality of food images;

extracting, from the plurality of food images, food information relating to types and served states of foods included in the food images and an edible portion of each food included in the food images;

calculating an area ratio between the edible portion of a same kind of food extracted from the plurality of food images; and converting the area ratio of each food into a volume ratio using conversion information corresponding to the food whose area ratio is to be converted from among conversion information corresponding to each type and served state of food based on the food information.

\* \* \* \* \*